United States Patent
Zanella et al.

(10) Patent No.: US 9,974,819 B2
(45) Date of Patent: May 22, 2018

(54) EXTRACTS OF MICROALGAE AND THEIR APPLICATION

(75) Inventors: Lorenzo Zanella, Venice (IT); Paolo Pertile, San Pietro Viminario (IT); Michele Massironi, Padua (IT); Marco Massironi, Padua (IT); Elisa Caviola, Pieve d'Alpago (IT)

(73) Assignee: Cutech S.r.L., Padua (IT)

( * ) Notice: Subject to any disclaimer, the term of this patent is extended or adjusted under 35 U.S.C. 154(b) by 782 days.

(21) Appl. No.: 13/883,193

(22) PCT Filed: Oct. 13, 2011

(86) PCT No.: PCT/EP2011/067945
§ 371 (c)(1),
(2), (4) Date: Sep. 9, 2013

(87) PCT Pub. No.: WO2012/052356
PCT Pub. Date: Apr. 26, 2012

(65) Prior Publication Data
US 2014/0010838 A1    Jan. 9, 2014

(30) Foreign Application Priority Data
Oct. 19, 2010   (EP) ..................................... 10013751

(51) Int. Cl.
| | | |
|---|---|---|
| *A61K 36/02* | (2006.01) | |
| *A61K 8/97* | (2017.01) | |
| *A61Q 5/00* | (2006.01) | |
| *A61Q 7/00* | (2006.01) | |
| *A61Q 7/02* | (2006.01) | |
| *A61Q 19/00* | (2006.01) | |
| *A61Q 19/02* | (2006.01) | |
| *A61Q 19/04* | (2006.01) | |
| *A61Q 19/08* | (2006.01) | |
| *A61K 8/99* | (2017.01) | |

(52) U.S. Cl.
CPC .............. *A61K 36/02* (2013.01); *A61K 8/975* (2013.01); *A61K 8/99* (2013.01); *A61Q 5/00* (2013.01); *A61Q 7/00* (2013.01); *A61Q 7/02* (2013.01); *A61Q 19/00* (2013.01); *A61Q 19/02* (2013.01); *A61Q 19/04* (2013.01); *A61Q 19/08* (2013.01)

(58) Field of Classification Search
None
See application file for complete search history.

(56) References Cited

U.S. PATENT DOCUMENTS

| | | | | |
|---|---|---|---|---|
| 5,620,962 A | * | 4/1997 | Winget | ................ A61K 9/0014 514/25 |
| 2007/0196893 A1 | * | 8/2007 | Weiss | .................... A61K 8/975 435/67 |

FOREIGN PATENT DOCUMENTS

| | | | | |
|---|---|---|---|---|
| EP | 2193785 A2 | | 9/2010 | |
| FR | 2847907 A1 | * | 6/2004 | ............... A61K 8/20 |
| JP | 11049695 A | * | 2/1999 | |
| JP | 11049695 A | * | 2/1999 | |
| JP | 11116431 A | * | 4/1999 | |
| JP | 2009179628 A | * | 8/2009 | |

OTHER PUBLICATIONS

Buttino et al. Marine Biology (1999) 134: 147-154.*
"Cosmetic" from American Heritage® Dictionary of the English Language, Fifth Edition. Copyright © 2011 by Houghton Mifflin Harcourt Publishing Company. Published by Houghton Mifflin Harcourt Publishing Company. [Retrieved on Jul. 29, 2016]. Retrieved from the internet: <URL: http://www.thefreedictionary.com/cosmetic>.*
Beattie et al: "XIII—The Polysaccharides Synthesized by Monodus subterraneus when Grown in Artificial Media under Bacteria-free Conditions," Proc. Roy. Soc. Edinburgh, vol. 68, 1962, pp. 171-185.
Khozin-Goldberg et al "The effect of phosphate starvation on the lipid and fatty acid composition of the fresh water eustigmatophyte Monodus subterraneus," Phytochemistry, Pergamon Press, Great Britain, vol. 67, issue No. 7, Apr. 1, 2006, pp. 696-701.

* cited by examiner

*Primary Examiner* — Amy L Clark
(74) *Attorney, Agent, or Firm* — Dilworth & Barrese, LLP

(57) ABSTRACT

Suggested are new extracts of microalgae selected from the group consisting of (i) *Monodus* sp. (ii) *Thalassiosira* sp. (iii) *Chaetoceros* sp. and/or (iv) *Chlorococcum* sp. obtainable by treating said microalgae with a solvent selected from the group consisting of $C_1$-$C_4$ aliphatic alcohols, ethyl acetate, water or their mixtures, removing the dissolved extracts from the residues and recovering the pure extracts from the solvent. The extracts show excellent properties particularly in modulating the metabolism of human skin and hair follicles.

14 Claims, No Drawings

EXTRACTS OF MICROALGAE AND THEIR APPLICATION

FIELD OF INVENTION

The present invention relates to the area of cosmetics and toiletries and refers to extracts of microalgae, processes and compositions for obtaining them, and their use in hair and skin care applications.

STATE OF THE ART

The cosmetics and toiletries industry has been devoting a rising interest in identifying natural compounds suitable to be employed for the preparation of body care products with a special attention to anti-aging products. The reduction of the birth rate experienced by industrialized economies and the prolongation of lifetime are increasing the impact of anti-aging products in the nutraceutical and cosmetic market.

Wrinkles represent the more visible symptom of skin aging, and cosmetics has been focusing its efforts on this issue for years. The decrease and structural modification of dermis collagen have been recognized as the main cause for skin wrinkles. Collagen stimulators have been actively screened among synthetic compounds and natural principles including microalgae extracts. However, also the epidermis can be considered for modulating treatments aimed at improving the moisturizing of the skin and aesthetics. In the epidermis, the basal undifferentiated keratinocytes continuously proliferate by alimenting the upper cell layers. These epidermis strata of cells progressively move towards the skin surface, by differentiating to corneocytes. The corneocytes are dead cells, of which the superficial stratum corneum is composed, and they are finally removed by desquamation. This continuous production and loss of epidermis cells constitutes the perpetual renewal of the skin. A forced elimination of the horny layer accelerates the renewal and makes it possible to combat aging, pimple formation and reduction of the aesthetic impact of scars. The forced and accelerate renewal of epidermis can also be required for the treatment of several skin disorders.

Among the primary functions of the epidermal stratum corneum, however, the prevention of water loss from the skin assumes a relevant importance. The insufficient thickness of the stratum corneum can induce a fragile and irritable condition in the skin also associated with xerosis and intense itching in the most severe cases. The balanced stimulation of the keratinocyte differentiation may enforce the epidermal horny layer, improving skin hydration and favoring health and smoothness of the skin.

On the one hand, some emerging economies, such as Brazil, are strongly contributing to the growth of the global cosmetic market with a high demand for skin care, hair care and fragrances. While the Western world considers anti-aging to be a major criterion for defining beauty, the same is associated to skin color in several Asian countries. Melanocytes are the cells specifically responsible for the melanin production in the skin and its annexes. Potential modulators of the melanin biosynthesis have to be considered to be of a high interest for both cosmetic and medical applications. Skin lightening cosmetics meet the interest of an increasing number of consumers by responding to the aesthetic desires of many people in Japan and in other Asian countries. However, skin lightening products are also applied in the treatment of skin disorders, such as, for example, the melasma, a skin condition in which brown patches occur primarily on the cheekbones, forehead and upper lip. This problem is more frequent among people having a coloured skin, including Asians. Among customers in the Western world, skin lightening products are appreciated also to prevent or inhibit face spots, including brown spots and freckles, and consist of anti-aging features.

On the other hand, the compounds suitable to produce the positive modulation of melanogenesis as well find wide cosmetic applications. Many people wish to tan their naturally pale skin colour and develop skin pigmentation without being exposed to solar radiation. In addition, some people have the desire to obtain a more intense and homogeneous hair colour. For this reason, very safe and effective skin and hair dying browning agents are necessary.

On this side, particular relevance is assumed by stimulating agents effective on melanogenesis of the hair pigmentary unit. Although there are important differences between the melanocyte metabolism in the hair follicle and in the skin, the discovery of natural modulators of this biological function present potential applications in both these organs. The prevention of hair whitening represents a very important aim for cosmetics, involving at the same time the beauty and the anti-aging sectors.

Treatments related to problems of the hair follicle, primarily hair loss and pigmentation issues, account for a total market of more than 10 billion US$ annually despite a lack of truly effective solutions. Hair loss represents the main problem to be solved and, presently, the 5-alpha-reductase inhibitors are considered the more active agents. 5-alpha-reductase is the key enzyme involved in the transformation of testosterone to dihydrotestosterone (DHT), considered the main steroid compound responsible for hair loss in the androgenetic alopecia. The active products, commercially available as Minoxidil (Rogaine), Finasteride (Propecia) and Dutasteride (Avodart), have to be administered under medical surveillance and cannot be used to treat pregnant women. They can produce several undesired effects while giving satisfactory responses in a limited part of treated subjects. Herbal preparations claiming to induce hair growth are available at a low cost, but their effectiveness is usually very limited.

On the other hand, also unwanted hair represents a relevant cosmetic issue, and the disclosure of new non-toxic agents inhibiting hair growth would find relevant applications. Modern lifestyle, characterized by sedentary work often associated with wrong nutritional behavior, has broadly promoted an excessive accumulation of body fat. Many people suffer from this problem with heavy consequences not only on their look and social relationships, but also on their health and life expectation. There are few solutions on this regard apart from severe slimming diets, fatiguing exercises, or dangerous and invasive interventions of aesthetic surgery. On the other hand, people having a normal weight can also be affected by fat deposition localised in the skin subcutis of particular body regions. Cellulite, for instance, can be considered a typical problem related with this unbalanced fat metabolism, scientifically defined as "lipodystrophy" or "edematous-fibrosclerotic panniculopathy". Very few cosmetic treatments are presently available for reducing the subcutaneous fatty layer, also referred to as subcutis. The cosmetics industry is very interested in the disclosure of effective compounds suitable to prevent the general accumulation of fat in the body, as well as to promote lipolysis in the subcutaneous tissue of the skin.

The prior art related to exploitation of microalgae in the field of cosmetics offers several examples, but very few with regard to the species considered here. WO 1989/000606 describes the use of obligately and facultatively marine eukaryotic microorganisms for the production of Omega-3 (n-3) fatty acids that may be used in food, cosmetic, and pharmaceutical products. Apart from the specific heterotrophic culture technique proposed, this invention suggested the exploitation of microalgae as a source of compounds, in particular n-3 fatty acids, for body treatment purposes. Some species are explicitly suggested as microalgae of interest, such as the diatom *Nitzschia* sp. and the dinoflagellate *Crypthecodinium cohni*.

The anti-free-radical activity of liquid extracts obtainable from Chlorophyceae, Prasinophyceae, Cryptophyceae, Bacillariophyceae (or diatoms) and Prymnesiophyceae was disclosed in FR 2657012 B1 (Secma) in 1990. The exploitability of *Chaetoceros* for cosmetic products is known since 1975 thanks to GB 1392131 A (Aubert et al.). Japanese patent JP 3-822959 B2 (Noevir KK) refers to skin lotions effective for preventing skin wrinkles comprising an extract of certain diatoms, particularly *Chaetoceros*. The extraction solvent is selected from ethanol, methanol, 1.3-butylene glycol, water and is used in a single form or a two or more mixed form. In a preferred embodiment, these solvents include an inorganic salt and a surfactant. U.S. Pat. No. 5,767,095 (Photonz) discloses topical anti-inflammatory compositions comprising monogalactosyl-dieicosapentanoyl glycerol obtained, among others, from *Chaetoceros* and *Thalassiosira*. According to EP 1808483 A1 (Cognis) *Chlorococcum citriforme* has been considered an interesting source of lutein for cosmetic applications. International patent application WO 1997/034489 A1 (Aquaculture Technology) refers to the use of extracts obtained from the marine algae *Chaetoceros* or *Thalassiosira* as anti-bacterially active agents, and to compositions containing such agents for use against pathogenic bacteria. International patent application WO 2010/0029115 A1 (LVHM Recherche) proposes the use of certain plant extracts, as, for example, obtained from *Thalassiosira* for reducing skin and hair pigmentation.

FR 2894473 A1 (Daniel Jouvance) discloses the use of preparations obtained from some microalgae (*Chromulina, Asterionella* and *Tetraselmis*) to inhibit the enzymes implied in the metabolism of fatty acids and lipids. Slimming preparations from several species of macro-algae are proposed in the Japanese patent JP 2000072642 A1 (Lion), however, no prior art is available with regard to fat metabolism modulation based on agents from the microalgae strains considered here.

The prior art is completely silent on the issue of skin stratum corneum modulation and lipolysis. The use of *Isochrysis* and *Tetraselmis* extracts for hair care products has been described in EP2168570A2 and EP 2193785 A2, respectively.

Therefore, the object of the present invention was to develop extracts based on renewable sources, more particularly on plants such as microalgae, suitable to modulate and to stimulate the metabolism of the human skin and hair follicles in order to achieve improvements in fighting and preventing hair loss and hair de-pigmentation. In particular, it was the object of the present invention to develop new extracts for cosmetic and, respectively, dermatological application, which simultaneously modulate, that means increase, improve and/or stimulate melanogenesis in human hair and skin;
growth or, in the alternative, inhibition of human hair and hair follicle growth;
collagen synthesis in the human dermis;
hyaluronic acid synthesis in the human dermis;
keratinocyte differentiation and modulation of the horny layer in the human epidermis,
stimulation on cell proliferation, more particularly stimulation of melanocyte proliferation;
improvement of wound healing, more particularly stimulation of fibroblast and keratinocyte proliferation; and
improvement of lipolysis.

DESCRIPTION OF THE INVENTION

Object of the present invention are extracts of microalgae selected from the group consisting of
(i) *Monodus* sp.
(ii) *Thalassiosira* sp.
(iii) *Chaetoceros* sp. and/or
(iv) *Chlorococcum* sp.
obtainable by treating said microalgae with a solvent selected from the group consisting of $C_1$-$C_4$ aliphatic alcohols, ethyl acetate, water or their mixtures, removing the dissolved extracts from the residues and recovering the pure extracts from the solvent.

Surprisingly, it was observed that the aforementioned extracts exhibit superior properties when compared with products obtained from the market with respect to the desired modulation of human skin and hair follicles, in particular with respect to melanogenesis, hair follicle growth or, in the alternative, inhibition of hair growth, collagen and hyaluronic acid synthesis, keratinocyte differentiation, melanocyte proliferation and in association with this effect, the improvement of wound healing, and, finally, the improvement of lipolysis. The invention encompasses the observation that the performance of the extracts is seriously linked to the nature of the extractant. In other words, different solvents result in extracts of different compositions and different properties.

Microalgae

According to the present invention, four types of microalgae have been identified suitable to solve the complex profile explained above.

*Monodus* sp.

*Monodus* sp., belonging to the class Eustigmatophyceae, stands for a class of microalgae rich in polyunsaturated fatty acids. The preferred strain is *Monodus subterraneus* (also known as *Monodopsis subterranea*), and in particular the strain CCAP 848/1 obtainable from the Culture Collection of Algae and Protozoa managed by the Scottish Association for Marine Science is preferably used (also registered in other collections as ATCC 30593; UTEX 151 and SAG 848-1).

*Thalassiosira* sp.

Among the various strains of *Thalassiosira*, also belonging to the class of Bacillariophyceae, *Thalassiosira pseudonana* is the best known species of marine centric diatom. It was chosen as the first eukaryotic marine phytoplankton for whole genome sequencing. *T. pseudonana* was selected for this study, because it is a model for diatom physiology studies and belongs to a genus widely distributed throughout the world's oceans, and has a relatively small genome at 34 mega base pairs. In particular, strain CS173 obtainable from the Australian CSIRO collection (also registered as CCMP1335 at the Provasoli-Guillard National Centre for Culture of Marine; NEPCC58 at the Canadian Centre for the Culture of Microorganisms) is preferably used for our purposes. This clone was originally collected in 1958 from Moriches Bay (Long Island, N.Y.) and has been maintained continuously in culture.

*Thalassiosira weissflogii* is a large diatom (6-20 µm×8-15 µm) that is used in the shrimp and shellfish larviculture industry. This algae is considered by several hatcheries to be the single best algae for larval shrimp. Its cell size is 16 times the biomass of *Chaetoceros* and 3 times the biomass of *Tetraselmis*. During the winter this algae measures about 15 microns but shrinks to about 5 microns during the summer. The color of TW varies from brown to green to yellow depending on the amount of chlorophyll in the culture. This color change does not in any way affect the quality of the algae. All these strains of *Thalassiosira* microalgae are suitable as starting materials in order to obtain the extracts according to the present invention.

*Chaetoceros* sp.

*Chaetoceros*, belonging to the class of Bacillophyceae, is probably the largest genus of marine plankton, more particularly diatoms with approximately 400 species described. Although a large number of these descriptions are no longer valid. It is often very difficult to distinguish between different *Chaetoceros* species. Several attempts have been made to restructure this large genus into subgenera, and this work is still in progress. However, most of the effort to describe species has been focused in boreal areas, and the genus is cosmopolitan, so there are probably a large number of tropical species still undescribed. The following compilation illustrates suitable strains of *Chaetoceros* with respect to the present invention:

*Chaetoceros abnormis* A. I. Proshkina-Lavrenko
*Chaetoceros aculeatus* I. V. Makarova
*Chaetoceros adelianus* E. E. Manguin
*Chaetoceros aduncus* I. N. Sukhanova
*Chaetoceros equatorialis* var. *antarcticus* Manguin
*Chaetoceros aequatorialis* Cleve
*Chaetoceros affinis* f. *pseudosymmetricus* (E. Steemann Nielsen) M. Torrington-Smith
*Chaetoceros affinis* f. *parallelus* M. Thorrington-Smith
*Chaetoceros affinis* f. *inaequalis* M. Thorrington-Smith
*Chaetoceros affinis* Lauder
*Chaetoceros amanita* A. Cleve-Euler
*Chaetoceros anastomosans* Grunow
*Chaetoceros angularis* Schütt
*Chaetoceros angulatus* F. Schütt
*Chaetoceros anostomosans* var. *speciosus* F. Schütt
*Chaetoceros armatus* T. West
*Chaetoceros astrabadicus* A. Henckel
*Chaetoceros atlanticus* var. *compactus* (F. Schütt) P. T. Cleve
*Chaetoceros atlanticus* var. *neapolitanus* (Schroeder) Hustedt
*Chaetoceros atlanticus* var. *tumescens* A. Grunow
*Chaetoceros atlanticus* Cleve
*Chaetoceros atlanticus* f. *audax* (F. Schütt) H. H. Gran
*Chaetoceros atlanticus* var. *cruciatus* (G. Karsten) M. Thorrington-Smith
*Chaetoceros audax* F. Schütt
*Chaetoceros bacteriastrius* G. C. Wallich
*Chaetoceros bacteriastroides* f. *imbricatus* (L. A. Mangin) M. Thorrington-Smith
*Chaetoceros bacteriastroides* G. H. H. Karsten
*Chaetoceros bermejense* D. U. Hernandez-Becerril
*Chaetoceros bisetaceus* J. Schumann
*Chaetoceros borealis* J. W. Bailey
*Chaetoceros borealoides* H. L. Honigmann
*Chaetoceros breve* F. Schütt
*Chaetoceros brevis* Schütt
*Chaetoceros brussilowi* A. Henckel
*Chaetoceros buceros* G. H. H. Karsten
*Chaetoceros buceros* Karsten
*Chaetoceros bulbosus* (Ehrenberg) Heiden
*Chaetoceros bulbosus* f. *cruciatus* (G. Karsten) H. Heiden
*Chaetoceros bulbosus* f. *schimperana* (G. Karsten) H. Heiden
*Chaetoceros bungei* Honigmann
*Chaetoceros calcitrans* f. *pumilus* Takano
*Chaetoceros californicus* A. Grunow
*Chaetoceros capense* G. H. H. Karsten
*Chaetoceros caspicus* C. E. H. Ostenfeld
*Chaetoceros caspicus* var. *karianus* A. Henckel
*Chaetoceros caspicus* f. *pinguichaetus* A. Henckel & P. Henckel
*Chaetoceros castracanei* Karsten
*Chaetoceros castracanei* G. H. H. Karsten
*Chaetoceros ceratospermus* var. *minor* A. F. Meunier
*Chaetoceros ceratosporus* var. *brachysetus* Rines & Hargraves
*Chaetoceros ceratosporus* Ostenfeld
*Chaetoceros chunii* G. H. H. Karsten
*Chaetoceros cinctus* Gran
*Chaetoceros clavigera* C. E. H. Ostenfeld
*Chaetoceros clavigerus* A. Grunow
*Chaetoceros clevei* F. Schütt
*Chaetoceros coarctatus* Lauder
*Chaetoceros cochleus* F. Schütt
*Chaetoceros compactus* F. Schütt
*Chaetoceros compressus* var. *gracilis* F. Hustedt
*Chaetoceros compressus* var. *hirtisetus* J. E. B. Rines & P. E. Hargraves
*Chaetoceros concavicorne* Mangin
*Chaetoceros confervoides* J. Ralfs
*Chaetoceros confusus* S. L. VanLandingham
*Chaetoceros constrictus* Gran
*Chaetoceros convolutus* Castracane
*Chaetoceros convolutus* f. *trisetosus* Brunel
*Chaetoceros convolutus* f. *volans* L. I. Smirnova
*Chaetoceros cornutus* G. Leuduger-Fortmorel
*Chaetoceros coronatus* Gran
*Chaetoceros costatus* Pavillard
*Chaetoceros crenatus* (C. G. Ehrenberg) T. Brightwell
*Chaetoceros crinitus* Schütt
*Chaetoceros criophilus* Castracane
*Chaetoceros cruciatus* G. H. H. Karsten
*Chaetoceros curvatus* Castracane
*Chaetoceros curvisetus* Cleve
*Chaetoceros dadayi* Pavillard
*Chaetoceros danicus* Cleve
*Chaetoceros debilis* Cleve
*Chaetoceros decipiens* f. *singularis* H. H. Gran
*Chaetoceros decipiens* Cleve
*Chaetoceros delicatulus* C. E. H. Ostenfeld
*Chaetoceros densus* Cleve
*Chaetoceros diadema* (Ehrenberg) Gran
*Chaetoceros dichaeta* f. *unicellularis* H. Heiden
*Chaetoceros dichaetus* Ehrenberg
*Chaetoceros dichaetus* var. *polygonus* (F. Schütt) H. Heiden
*Chaetoceros didymus* var. *praelongus* E. J. Lemmermann
*Chaetoceros didymus* f. *aestivus* H. H. Gran
*Chaetoceros didymus* f. *autumnalis* H. H. Gran
*Chaetoceros didymus* C. G. Ehrenberg
*Chaetoceros difficilis* Cleve
*Chaetoceros distichus* F. Schütt
*Chaetoceros distinguendus* E. J. Lemmermann
*Chaetoceros diversicurvatus* Van Goor
*Chaetoceros diversus* var. *mediterraneus* J. L. B. Schroder
*Chaetoceros diversus* Cleve

*Chaetoceros eibenii* (Grunow) Meunier
*Chaetoceros elmorei* Boyer
*Chaetoceros elongatus* Honigmann
*Chaetoceros exospermus* Meunier
*Chaetoceros externus* Gran
*Chaetoceros fallax* Prosckina-Lavrenko
*Chaetoceros femur* F. Schütt
*Chaetoceros filiferus* G. H. H. Karsten
*Chaetoceros filiforme* Meunier
*Chaetoceros flexuosus* Mangin
*Chaetoceros fragilis* Meunier
*Chaetoceros furca* var. *macroceras* J. L. B. Schroder
*Chaetoceros furcellatus* J. W. Bailey
*Chaetoceros fusus* F. Schütt
*Chaetoceros galvestonense* Collier & Murphy
*Chaetoceros gastridius* (C. G. Ehrenberg) T. Brightwell
*Chaetoceros gaussii* Heiden & Kolbe
*Chaetoceros glacialis* A. Henckel
*Chaetoceros glandazii* Mangin
*Chaetoceros gobii* A. Henckel
*Chaetoceros gracilis* Pantocsek
*Chaetoceros grunowii* F. Schütt
*Chaetoceros hendeyi* Manguin
*Chaetoceros hispidus* var. *monicae* A. Grunow
*Chaetoceros hohnii* Graebn. & Wujek
*Chaetoceros holsaticus* Schütt
*Chaetoceros ikari* B. V. Skvortzov
*Chaetoceros imbricatus* Mangin
*Chaetoceros incurvus* var. *umbonatus* Castracane
*Chaetoceros incurvus* Bailey
*Chaetoceros indicus* Karsten
*Chaetoceros ingolfianus* Ostenfeld
*Chaetoceros intermedius* A. Henckel
*Chaetoceros karianus* Grunow
*Chaetoceros karyanus* A. Henckel
*Chaetoceros knipowitschii* A. Henckel
*Chaetoceros laciniosus* Schiit
*Chaetoceros laciniosus* f. *protuberans* M. Thorrington-Smith
*Chaetoceros laciniosus* f. *pelagicus* H. H. Gran
*Chaetoceros lauderi* Ralfs
*Chaetoceros leve* F. Schütt
*Chaetoceros littorale litorale* E. J. Lemmermann
*Chaetoceros lorenzianus* var. *forceps* A. F. Meunier
*Chaetoceros lorenzianus* Grunow
*Chaetoceros malygini* A. Henckel
*Chaetoceros medius* F. Schütt C
*Chaetoceros meridiana* (F. Schütt) G. Karsten
*Chaetoceros mertensii* H. L. Honigmann
*Chaetoceros messanense* Castracane C
*Chaetoceros minimus* (Levander) D. Marino, G. Giuffre, M. Montresor & A. Zingone
*Chaetoceros misumensis* H. H. Gran & K. Yendo
*Chaetoceros mitra* (J. W. Bailey) Cleve
*Chaetoceros muelleri* var. *duplex* E. J. Lemmermann
*Chaetoceros muelleri* var. *subsalsum* J. R. Johansen & S. Rushforth
*Chaetoceros muelleri* E. J. Lemmermann
*Chaetoceros muellerii* var. *subsalsus* J. R. Johansen & Rushforth
*Chaetoceros nansenii* A. Henckel
*Chaetoceros natatus* E. E. Manguin
*Chaetoceros neglectus* Karsten
*Chaetoceros neobulbosus* T. V. Desikachary, S. Gowthaman & Y. Latha
*Chaetoceros neocompactus* S. L. VanLandingham
*Chaetoceros neogracile* S. L. VanLandingham
*Chaetoceros neupokojewii* A. Henckel
*Chaetoceros nipponicus* J. Ikari
*Chaetoceros odontella* (C. G. Ehrenberg) G. L. Rabenhorst
*Chaetoceros okamurae* var. *tetrasetus* J. Ikari
*Chaetoceros okamurae* J. Ikari
*Chaetoceros ostenfeldii* P. T. Cleve
*Chaetoceros pachtussowii* A. Henckel
*Chaetoceros pachyceros* R. Margalef
*Chaetoceros pacificus* J. lkari
*Chaetoceros paradoxus* Cleve
*Chaetoceros paradoxus* var. *luedersii* Engler
*Chaetoceros parvus* F. Schütt
*Chaetoceros paulsenii* f. *robustus* A. Henckel
*Chaetoceros pavillardii* J. lkari
*Chaetoceros pelagicus*
*Chaetoceros pendulus* Karsten
*Chaetoceros perpusillus* Cleve
*Chaetoceros peruvianus* var. *victoriae* Karsten
*Chaetoceros peruvianus* var. *gracilis* J. L. B. Schroder
*Chaetoceros peruvianus* Brightwell
*Chaetoceros peruvianus* var. *robustum* P. T. Cleve
*Chaetoceros peruvianus* var. *suadivae* Karsten
*Chaetoceros peruvianus* f. *volans* (F. Schütt) C. E. H. Ostenfeld
*Chaetoceros peruvianus* f. *robustus* (P. T. Cleve) C. E. H. Ostenfeld
*Chaetoceros phuketensis* J. E. B. Rines, P. Boonruang & E. C. Theriot
*Chaetoceros pingue* A. Henckel
*Chaetoceros pinguichaetus* A. Henckel & P. Henckel
*Chaetoceros pliocenus* J.-J. Brun
*Chaetoceros protuberans* H. S. Lauder
*Chaetoceros pseudoaurivillii* J. lkari
*Chaetoceros pseudocrinitus* Ostenfeld
*Chaetoceros pseudocurvisetus* Mangin
*Chaetoceros pseudodichaeta* J. lkari
*Chaetoceros pundulus* G. H. H. Karsten
*Chaetoceros radians* F. Schütt
*Chaetoceros radicans* F. Schütt
*Chaetoceros recurvatus* f. *robustus* Henckel
*Chaetoceros recurvatus* Henckel
*Chaetoceros robustus* (P. T. Cleve) C. E. H. Ostenfeld
*Chaetoceros rostratus* Lauder
*Chaetoceros russanowi* A. Henckel
*Chaetoceros salsugineus* Takano
*Chaetoceros saltans* P. T. Cleve
*Chaetoceros schmidtii* C. E. H. Ostenfeld
*Chaetoceros schuettii* f. *oceanicus* H. H. Gran
*Chaetoceros secundus* P. T. Cleve
*Chaetoceros seiracanthus* Gran
*Chaetoceros sessile* Grøntved
*Chaetoceros setoense* J. Ikari
*Chaetoceros seychellarus* G. H. H. Karsten
*Chaetoceros seychellarus* var. *austral* E. E. Manguin
*Chaetoceros siamense* C. E. H. Ostenfeld
*Chaetoceros similis* Cleve
*Chaetoceros simplex* C. E. H. Ostenfe/d C
*Chaetoceros skeleton* F. Schütt
*Chaetoceros socialis* f. *radians* (F. Schütt) A. I. Proshkina-Lavrenko
*Chaetoceros socialis* Lauder
*Chaetoceros socialis* var. *autumnalis* Prosckina-Lavrenko
*Chaetoceros sedowii* A. Henckel
*Chaetoceros strictus* G. H. H. Karsten
*Chaetoceros subcompressus* J. L. B. Schroder
*Chaetoceros subsalsus* Lemmermann

*Chaetoceros subsecundus* (Grunow ex Van Heurck) Hustedt
*Chaetoceros subtilis* Cleve
*Chaetoceros sumatranus* Karsten
*Chaetoceros tenuissimus* A. F. Meunier
*Chaetoceros teres* f. *spinulosus* H. H. Gran
*Chaetoceros teres* Cleve
*Chaetoceros tetrachaeta* Ehrenberg
*Chaetoceros tetras* G. H. H. Karsten
*Chaetoceros tetrastichon* Cleve
*Chaetoceros thienemannii* Hustedt
*Chaetoceros throndsenii* var. *trisetosus* Zingone
*Chaetoceros throndsenii* var. *throndsenia* D. Marino, M. Montresor & A. Zingone
*Chaetoceros throndsenii* (Marino, Montresor, & Zingone) Marino, Montresor & Zingone
*Chaetoceros tortissimus* H. H. Gran
*Chaetoceros transisetus* J. R. Johansen & J. S. Boyer
*Chaetoceros vanheurckii* H. H. Gran
*Chaetoceros vermiculus* F. Schütt
*Chaetoceros villosus* Kützing
*Chaetoceros vistulae* C. Apstein
*Chaetoceros volans* F. Schütt
*Chaetoceros weissflogii* F. Schütt
*Chaetoceros wighamii* Brightwell
*Chaetoceros willei* Grunow
*Chaetoceros zachariasi* var. *longus* H. L. Honigmann
*Chaetoceros zachariasii* var. *variatus* H. L. Honigmann
*Chaetoceros zachariasii* var. lotus H. L. Honigmann
*Chaetoceros zachariasii* Honigmann
*Chaetoceros ziwolkii* A. Henckel Two different strains were studied for the experiments herein reported: the first is a *Chaetoceros* sp. of uncertain origin, while the second one is *Chaetoceros calcitrans* f. *pumilus*, a marine strain isolated in 1960 from marine waters at Urayasu (Chiba Prefecture, Japan) near Umbayashi. This latter one is archived as strain CCAP 1010/11 at the Culture Collection of Algae and Protozoa (CCAP) managed by the Scottish Association for Marine Science (also registered in other collections as PLY537; CCMP1315; NEPCC 590).

*Chlorococcum* sp.

*Chlorococcum* is a genus of algae in the family Chlorococcaceae. The following compilation illustrates suitable strains of *Chlorococcum* with respect to the present invention:

C. acidum
C. aegyptiacum
C. botryoides
C. choloepodis
C. citriforme
C. costatozygotum
C. diplobionticum
C. dissectum
C. echinozygotum
C. elbense
C. elkhartiense
C. ellipsoideum
C. hypnosporum
C. infusionum
C. isabeliense
C. lobatum
C. macrostigmatum
C. minimum
C. minutum
C. novae-angliae
C. oleofaciens
C. olivaceum
C. pamirum
C. pinguideum
C. polymorphum
C. pseudodictyosphaerium
C. pyrenoidosum
C. refringens
C. salinum
C. schizochiamys
C. schwarzii
C. submarinum
C. tatrense
C. vacuolatum For the present study, two different strains were used: the first is a *Chloroccum* sp. of uncertain origin, while the second one is *Chlorococcum minutum*, a freshwater microalgae archived as strain CCAP 213/7 (SAG 213-7; SAG 21.95; UTEX 117; CCAO 290) at the Culture Collection of Algae and Protozoa (CCAP) managed by the Scottish Association for Marine Science. This latter one was isolated by Bold from soil in India.

*Cholorococcum minutum* is currently regarded as a taxonomic synonym of the following species (Guiry, M. D. & Guiry, G. M. 2011. AlgaeBase. World-wide electronic publication, National University of Ireland, Galway. http://www.algaebase.org; searched on 7 Sep. 2011):

*Chlorococcum scabellum* Deason& Bold 1960
*Chlorococcum aureum* Archibald& Bold 1970
*Chlorococcum reticulatum* Archibald& Bold 1970
*Chlorococcum sphacosum* Archibald& Bold 1970
*Chlorococcum typicum* Archibald& Bold 1970

Extraction Process

Another object of the present invention relates to a process for obtaining extracts of (i) *Monodus* sp.
(ii) *Thalassiosira* sp.
(iii) *Chaetoceros* sp. and/or
(iv) *Chlorococcum* sp.

comprising the following steps:

(a) bringing said microalgae in contact with a solvent selected from the group consisting of $C_1$-$C_4$ aliphatic alcohols, ethyl acetate, water or their mixtures in an amount suitable to effect that the actives move into the solvent phase, optionally at elevated temperatures,
(b) removing the dissolved extract from the residue, and
(c) recovering the pure extract from the solvent.

Basically, the extracts according to the present invention may be prepared by methods known per se, for example, by aqueous, organic or aqueous/organic extraction of the microalgae using the solvents explained above. Suitable extraction processes are any conventional extraction processes such as maceration, re-maceration, digestion, agitation maceration, vortex extraction, ultrasonic extraction, counter current extraction, percolation, re-percolation, evacolation (extraction under reduced pressure), diacolation and solid/liquid extraction under continuous reflux. Percolation is advantageous for industrial uses. Any size reduction methods known to the expert, for example, freeze grinding, may be used. Preferred solvents for the extraction process are methanol, ethanol, isopropyl alcohol, ethyl acetate and water (preferably hot water with a temperature above 80° C., and more particularly above 95° C.) or mixtures of said organic solvents and water, more particularly, low molecular weight alcohols with more or less high water contents. An extraction with methanol, ethanol and water-containing mixtures thereof is particularly preferred. The extraction process is generally carried out at temperatures of from about 20 to about 100° C., and preferably from about 50 to about 70° C.

In one preferred embodiment, the extraction process is carried out in an inert gas atmosphere to avoid the oxidation of the ingredients of the extract. This is particularly important where extraction is carried out at temperatures above 40° C. The extraction times are selected by the expert depending on the starting material, the extraction process, the extraction temperature, and the ratio of solvent to raw material, etc. After the extraction process, the crude extracts obtained may optionally be subjected to other typical steps, such as, for example, purification, concentration and/or decoloration. If desired, the extracts thus prepared may be subjected, for example, to the selective removal of individually unwanted ingredients. The extraction process may be carried out to any degree, but is usually continued to exhaustion. Typical yields (=extract dry matter based on the quantity of raw material used) in the extraction of the starting materials are of the order of from about 1 to about 50%, preferably from about 2 to about 20%, and more preferably from about 5 to about 10% b.w.—calculated on the starting materials.

In the following, three typical processes for obtaining the extracts according to the invention are described in more detail:

Methanol or Ethanol or Isopropyl Alcohol or Ethyl Acetate Extraction Process: Single Solvent Extraction Each gram of dry biomass was extracted by treatment with 100 ml of solvent, stirring the suspension at room temperature for 16 hours in the dark;
the residual cell material was separated from the extract by centrifugation at 2000G for 15 minutes;
the residual biomass was washed by suspending it in 50 ml of solvent;
the cell material was separated from the washing solvent by centrifugation at 2000G for 15 minutes;
the residual biomass was washed again by suspending it in 50 ml of solvent;
the cell material was separated from the washing solvent by centrifugation at 2000G for 15 minutes;
the firstly collected extract and the washing solvent volumes were mixed, and the resulting extract was considered to have a conventional concentration of 5000 μg/ml (1000 mg of dry algae in 200 ml of solvent).

Two-Step Sequential Extraction: Ethanol>Water

In order to obtain a first separation between the more lipophilic compounds and the hydrophilic ones, a two-step extraction protocol was performed by treating the dry algal material with ethanol as described for the single solvent extraction, and then processing again the residual cell material by using the water as solvent. The described protocol provides that the same cell material sample is sequentially treated with different solvents, but only the first extract of the sequence was obtained from the integral cell material; for this reason it is referred to as "direct extract" (in this case direct ethanol extract). The subsequent extracts prepared from the residual cell material, progressively less reach in compounds, hereinafter are called "sequential extract" (in this case sequential water extract).

Three-Step Sequential Extraction: Ethyl Acetate>Absolute Ethanol>Water

This three-step extraction protocol was performed in order to obtain a better separation of the lipophilic compounds from the weakly lipophilic and the hydrophilic ones. The technical procedure was the same as the extraction protocol described for the single solvent extraction, but in this case the first extraction was performed using ethyl acetate, and then the extraction process was completely repeated twice, changing the extraction solvents at each passage (ethyl acetate>ethanol>water).

The microalgae composition is very rich in active compounds, sometimes suitable to produce opposite effects on the same target tissue. As a result, the biological activity of each extract strictly depends on both the microalgae strain and the extraction process adopted. Surprisingly it happens, for instance, that, while the extraction of *Chaetoceros* cell material using the direct ethanol or direct isopropyl alcohol way leads to extracts which inhibit unwanted hair growth, the sequential-ethanol extract obtained from the same cell material according to the three-step sequential extraction shows the opposite effect, that means it stimulates the growth of hair follicles.

INDUSTRIAL APPLICATION

Another object of the present invention is directed at cosmetic compositions comprising extracts of microalgae selected from the group consisting of
(i) *Monodus* sp.
(ii) *Thalassiosira* sp.
(iii) *Chaetoceros* sp. and/or
(iv) *Chlorococcum* sp.
and a cosmetically acceptable carrier selected from the group consisting of $C_1$-$C_4$ aliphatic alcohols, polyols having 3 to 12 carbon atoms, oil components, water and their mixtures. Suitable carriers encompass, for example, ethanol, propanol, isopropyl alcohol, all isomeric forms of butanol, ethylene and/or propylene glycol and its dimers and trimers, glycerol, glucose, pentaerythritol and the like. Suitable oil components are disclosed in the following chapter.

The compositions may contain the extracts in amounts of from 0.001 to 35, preferably from 0.5 to 20, and more preferably from 2 to 10% b.w.—the amounts calculated on the dry matter of the extracts. The remaining parts are the carriers. Typically, the administration of the extracts takes place topically; however, it is also possible to use the extracts—especially after encapsulation—for oral uptake.

Cosmetic Compositions

Cosmetic compositions also encompass dermatological compositions and, in particular, compositions for treating human skin and hair. Said compositions may contain additional compounds such as, for example, surfactants, oil bodies, emulsifiers, superfatting agents, pearlising waxes, consistency factors, polymers, silicone compounds, waxes, stabilizers, antidandruff agents, biogenic agents, film formers, preservatives, perfume oils, dyes and the like as additional auxiliaries and additives.

Surfactants

Other preferred auxiliaries and additives are anionic and/or amphoteric or zwitterionic surfactants. Typical examples of anionic surfactants are soaps, alkyl benzenesulfonates, alkanesulfonates, olefin sulfonates, alkylether sulfonates, glycerol ether sulfonates, methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside and Mineralöladditive (Catalysts, Surfactants and Mineral Oil Additives)", Thieme Verlag, Stuttgart, 1978, pages 123-217. The percentage content of surfactants in the preparations may be from 0.1 to 10% by weight and is preferably from 0.5 to 5% by weight, based on the preparation.

Oil Components (Also Carriers)

Suitable oil bodies forming cosmetically acceptable carriers are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.), aliphatic or naphthenic hydrocarbons such as, for example, squalane, squalene or dialkylcyclohexanes, and/or mineral oils.

Emulsifiers

Other surfactants may also be added to the preparations as emulsifiers, including, for example:

products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;

$C_{12/18}$ fatty acid monoesters and diesters of addition products of 1 to 30 mol ethylene oxide onto glycerol;

glycerol mono- and diesters and sorbitan mono- and diesters of saturated and unsaturated fatty acids containing 6 to 22 carbon atoms and ethylene oxide addition products thereof;

addition products of 15 to 60 mol ethylene oxide onto castor oil and/or hydrogenated castor oil;

polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;

addition products of 2 to 15 mol ethylene oxide onto castor oil and/or hydrogenated castor oil;

partial esters based on linear, branched, unsaturated or saturated $C_{6/22}$ fatty acids, ricinoleic acid and 12-hydroxystearic acid and glycerol, polyglycerol, pentaerythritol, -dipentaerythritol, sugar alcohols (for example sorbitol), alkyl glucosides (for example methyl glucoside, butyl glucoside, lauryl glucoside) and polyglucosides (for example cellulose);

mono-, di and trialkyl phosphates and mono-, di- and/or tri-PEG-alkyl phosphates and salts thereof;

wool wax alcohols;

polysiloxane/polyalkyl polyether copolymers and corresponding derivatives;

mixed esters of pentaerythritol, fatty acids, citric acid and fatty alcohol and/or mixed esters of $C_{6-22}$ fatty acids, methyl glucose and polyols, preferably glycerol or polyglycerol, polyalkylene glycols and glycerol carbonate.

The addition products of ethylene oxide and/or propylene oxide onto fatty alcohols, fatty acids, alkylphenols, glycerol mono- and diesters and sorbitan mono- and diesters of fatty acids or onto castoroil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations.

Typical anionic emulsifiers are aliphatic $C_{12-22}$ fatty acids such as palmitic acid, stearic acid or behenic acid, for example, and $C_{12-22}$ dicarboxylic acids, such as azelaic acid or sebacic acid, for example. Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are what is referred to as betaines such as N-alkyl-N,N-dimethyl ammonium glycinates, for example, cocoalkyl dimethyl ammonium glycinate, N-acylaminopropyl-N,N-dimethyl ammonium glycinates, for example, cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Superfatting Agents

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Consistency Factors

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystea rates is preferably used.

Thickening Agents

Suitable thickeners are polymeric thickeners, such as Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates and electrolytes, such as sodium chloride and ammonium chloride.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar® CBS, Jaguar® C-17, Jaguar® C-16 of Celanese, quaternized ammonium salt polymers such as, for example, Mirapol® A-15, Mirapol® AD-1, Mirapol® AZ-1 of Miranol. Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Pearlising Waxes

Suitable pearlising waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxy-substituted carboxylic acids with fatty alcohols containing 6 to 22 carbon atoms, especially long-chain esters of tartaric acid; fatty compounds such as, for example, fatty alcohols, fatty ketones, fatty aldehydes, fatty ethers and fatty carbonates which contain in all at least 24 carbon atoms, especially laurone and distearylether; fatty acids such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Silicones

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Waxes and Stabilizers

Besides natural oils used, waxes may also be present in the preparations, more especially natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes. Metal salts of fatty acids such as, for example, magnesium, aluminium and/or zinc stearate or ricinoleate may be used as stabilizers.

Biogenic Agents

In the context of the invention, biogenic agents are, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, for example, prune extract, bambara nut extract, and vitamin complexes.

Film Formers

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Antidandruff Agents

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

Perfume Oils

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example, civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular composition. The compositions may be produced by standard hot or cold processes.

Capsules and Microcapsules

For oral uptake, encapsulation of the extracts represents a preferred embodiment. Usually encapsulation can take place by using gelatine as a matrix. It is also possible to prepare capsules by adding a gelling agent such as, for example, alginate to the extracts and drop the mixture into a bath of a calcium salt. Both methods lead to macro-capsules having a diameter of from about 1 cm to about 5 cm which are toxicologically safe and suitable for consumption.

It may also be desired to encapsulate the extracts for the formulation of compositions which are developed for topical application. This can have different reasons: stabilisation against an interaction with other compounds in the formulation, protection against chemical degradation or simply for the preparation of a very aesthetica) product. For this purpose, usually microcapsules are applied. "Microcapsules" are understood to be spherical aggregates with a diameter of from about 0.1 to about 5 mm which contain at least one solid or liquid core surrounded by at least one continuous membrane. More precisely, they are finely dispersed liquid or solid phases coated with film-forming polymers, in the production of which the polymers are deposited onto the material to be encapsulated after emulsification and coacervation or interfacial polymerization. In another process, liquid active principles are absorbed in a matrix ("microsponge") and, as microparticles, may be additionally coated with film-forming polymers. The microscopically small capsules, also known as nanocapsules, can be dried in the same way as powders. Besides single-core microcapsules, there are also multiple-core aggregates, also known as microspheres, which contain two or more cores distributed in the continuous membrane material. In addition, single-core or multiple-core microcapsules may be surrounded by an additional second, third, etc., membrane. The membrane may consist of natural, semisynthetic or synthetic materials. Natural membrane materials are, for example, gum arabic, agar agar, agarose, maltodextrins, alginic acid and salts thereof, for example sodium or calcium alginate, fats and fatty acids, cetyl alcohol, collagen, chitosan, lecithins, gelatin, albumin, shellac, polysaccharides, such as starch or dextran, polypeptides, protein hydrolyzates, sucrose and waxes. Semisynthetic membrane materials are inter alia chemically modified celluloses, more particularly cellulose esters and ethers, for example cellulose acetate, ethyl cellulose, hydroxypropyl cellulose, hydroxypropyl methyl cellulose and carboxymethyl cellulose, and starch derivatives, more particularly starch ethers and esters. Synthetic membrane materials are, for example, polymers such as polyacrylates, polyamides, polyvinyl alcohol or polyvinyl pyrrolidone. Examples of known microcapsules are the following commercial products (the membrane material is shown in brackets) Hallcrest Microcapsules (gelatin, gum arabic), Coletica Thalaspheres (maritime collagen), Lipotec Millicapseln (alginic acid, agar agar), Induchem Unispheres (lactose, microcrystalline cellulose, hydroxypropylmethyl cellulose), Unicetin C30 (lactose, microcrystalline cellulose, hydroxypropylmethyl cellulose), Kobo Glycospheres (modified starch, fatty acid esters, phospholipids), Softspheres (modified agar agar) and Kuhs Probiol Nanospheres (phospholipids).

Non-Pharmaceutical Applications

In addition, the invention is also directed to a number of applications, in particular to the use of the extracts of microalgae selected from the group consisting of
(i) *Monodus* sp.
(ii) *Thalassiosira* sp.
(iii) *Chaetoceros* sp. and/or
(iv) *Chlorococcum* sp.
　　for the treatment of human hair;
　　for the treatment of human skin;
　　for modulating melanogenesis in human hair and/or human skin;
　　for the growth of human hair and hair follicles;
　　for inhibiting unwanted growth of human hair;
　　for fighting and preventing hair loss;
　　for improving and stimulating collagen synthesis in the human dermis;
　　for preventing and fighting skin aging;
　　for improving and stimulating glucosaminoglycans synthesis in human skin, in particular in dermis or epidermis;
　　for improving and stimulating keratinocyte differentiation in the human epidermis;
　　for modulating of the horny layer in the human epidermis;
　　for improving and stimulating the proliferation of dermal and epidermal cells and wound healing;
　　for improving and stimulating melanocyte proliferation;
　　for improving and stimulating lipolysis;
All these applications can be summarized under the expression "modulation" of human skin, particular the dermis, and of human hair, particular human hair follicles, in order to fight or prevent symptoms like hair loss or hair de-pigmentation or conditions of the skin associated with certain dysfunctions of the hair follicles such as, for example, pimples or inflammations.

In the following, the invention is illustrated—but not limited to—by various working examples.

EXAMPLES

A. General Remarks

In order to solve the complex problem underlying the present invention and to evaluate the biological properties of the microalgal constituents, it was necessary to decompose their biomasses by preparing complementary extracts and then submit each one to specific screening tests suitable to highlight their biological activities. Considering the huge biodiversity which characterizes microalgae, it can easily be understood how much relevant work was necessary in order to identify very few strains that are suitable to provide extracts exhibiting the desired properties. The claimed preparation of raw extracts is a simple, but effective way to separate the basic constituents of the algal biomass in relationship to their affinity for the adopted extracting solvent. Subject of this technical teaching is the demonstration that some innovative biological activities are present in the components of the considered species. The following experiments show how different biologically active extracts can be obtained from the same algal biomass and how they can be sequentially extracted by treating that biomass with subsequent exposition to different solvents.

In order to disclose exemplificative biological activities of the studied microalgae, various experiments with different extracts obtained from dried and powered biomass of

*Monodus* sp. (Class Eustigmatophyceae),
　　*Thalassiosira* sp. (Class Bacillariophyceae),
　　*Chaetoceros* sp. (Class Bacillariophyceae), and
　　*Chlorococcum* sp. (Class Chlorocaccaceae)
were conducted.

The extraction protocols were selected from many other technical solutions, and they have to be considered as truly exemplificative representations. According to the present invention, cell material of the aforementioned microalgae was extracted with a liquid extractant selected from the group consisting of ethyl acetate, isopropanol, ethanol, methanol and water.

The extractant can also comprise a mixture of two or more of the aforementioned solvents.

Hereinafter, the extract concentrations will be conventionally expressed as the ratio between the quantity (in weight) of cell material treated and the extractive solvent (in volume). For instance, by treating 1 g of dry powered microalgae with 200 ml of extractive solvent, 200 ml of extract at 5000 µg/ml (w/v) are obtained without regard for the quantity of compounds really solubilised in the solvent. This conventional concentration allows representing the quantity of microalgae effectively required to produce the experimental results described. However, the estimated dry weights of the extracts are reported in Table 1 and the real extract concentration can be calculated. As the composition of the microalgae may change in relation to culture methods and environmental conditions, also the extraction efficacy may change and the extract dry weights have to be considered as raw indications.

Quantity and quality of compounds present in the extracts may vary with respect to both solvent properties and preparation protocol. The selected algae strains showed a different refractoriness to release substances under action of the solvent, basically depending on the characteristics of their respective cell wall. In Table 1, the dry weights of the prepared extracts expressed as percentage of the related integral microalgae material are reported:

TABLE 1

Dry weight of the extracts expressed as percentage of the dry cell material

| Extract code | Chaetoceros sp. | Thalassiosira pseudonana | Monodus subterraneus | Chlorococcum sp. |
|---|---|---|---|---|
| Methanol | 46-58 | 39 | 19.5 | 18-28 |
| Ethanol | 32 | 27 | | 6.5 |
| Isopropyl alcohol | 22 | 15 | 2 | 3 |
| Ethyl acetate | 13-18 | 18 | 4 | 3-4 |
| Ethanol < Ethyl acetate | 22 | 18 | 5 | 5 |
| Water < Ethanol < Ethyl acetate | 34 | 22 | 16 | 34-44 |

| Extract code | Chaetoceros calcitrans | Chlorococcum minutum |
|---|---|---|
| Methanol | 54% | 24% |
| Ethanol | 22% | 16% |
| Isopropyl alcohol | 10% | 10% |
| Ethyl acetate | 9-12% | 5-8% |
| Ethanol < Ethyl acetate | 13% | 8-12% |
| Water < Ethanol < Ethyl acetate | 64% | 22% |

B. Activity of the Microalgae Extracts on Hair Follicle Growth

Examples 1 to 2

Activity of Direct Methanol (d-MeOH) Extract from *Chaetoceros* sp. on the Growth of Hair Follicles Hair follicles were taken from a single donor's scalp sample and transferred in sterile 24 well plates to be cultivated by using a modified Williams' Medium E. Cultivation took place for ten days, while the experimental treatment of the follicles started 24 hours from the beginning of the cultivation. Hair follicles were selected for the experiments after 18 h of cultivation. Only those follicles showing a good vital stage and a growth of not less than 0.2 mm were considered suitable to be maintained in culture. All experimental groups and the control were prepared comprising 12 follicles, plated in 24-well plates at a density of 3 hair follicles/well. The hair follicles showing evident signs of sufferance during the culture for reasons not dependent on the experimental treatment were excluded from the final analysis. The following experiments were conducted to demonstrate the activity of the direct-methanol extract (d-MeOH)—in this case obtained from dried biomass of *Chaetoceros* sp.—on hair follicle growth. Experimental culture media were supplemented by MeOH extract prepared from the *Chaetoceros* dry cell material in order to obtain two final concentrations corresponding to 0.1 and 1 µg/ml (=ppm). The growth performances observed in the treated hair follicles were compared to a control group cultured in the same culture medium free from extract supplement. The activity of the microalgae treatment is demonstrated by the increase of growth of the hair follicles expressed as a variation of the average elongation of each experimental group in comparison to the control group. The experiments were terminated after 9 days of cultivation (8 of treatment). The growth of the hair follicles was studied by microphotography and subsequently determined by image analysis. All hair follicles were photographed at day 5 and day 9 of culture, respectively. The experiments were replicated three times using hair follicles taken from three donors. The reported results were computed by pooling the data recorded from the hair follicles of the responsive donors, however, the number of the responsive donors was reported (Table 2).

TABLE 2

Growth of hair follicles - elongation expressed as % ratio of the control group performance. Data pooled from 2 out of 3 tested donors (responsiveness = 66%)

| Example | Sample | Amount | Average | Std. error | Total no. of HFs |
|---|---|---|---|---|---|
| 0 | Control | 0 | 100.00 | 3.09 | 36 |
| 1 | d-MeOH | 0.1 µg/ml | 103.18 | 4.82 | 22 |
| 2 | d-MeOH | 1.0 µg/ml | 110.30 | 3.63 | 21 |

The results indicate that the addition of the direct methanol extract leads to an increase in growth of the hair follicles, varying from +3 to +10% in comparison to the untreated group. The best response was obtained by treating the hair follicle with 1 µg/ml of extract.

Examples 3 to 4

Activity of Direct Ethanol (d-EtOH) Extract Obtained from *Chaetoceros calcitrans* f. *pumilus* on the Growth of Hair Follicles The experimental protocol previously described was adopted to study the activity of direct ethanol extract obtained from *Chaetoceros calcitrans* f. *pumilus* on the growth of hair follicles. The experiments were replicated twice using hair follicles taken from two donors. The reported results were computed by pooling the data recorded and are shown in Table 3.

TABLE 3

Growth of hair follicles - elongation expressed as % ratio of the control group performance Data pooled from 2 out of 2 tested donors (responsiveness = 100%)

| Example | Sample | Amount | Average | Std. error | Total no. of HFs | ANOVA |
|---|---|---|---|---|---|---|
| 0 | Control | 0 | 100.0 | 3.3 | 27 | — |
| 3 | d-EtOH | 0.1 µg/ml | 116.7 | 7.4 | 19.0 | $P < 0.05$ |
| 4 | d-EtOH | 1 µg/ml | 119.5 | 8.4 | 16.0 | $P < 0.05$ |

Direct ethanol extract stimulated hair follicle growth inducing an increase of elongation varying from +17% to +20%. Both results are significant on a statistical basis, however, the best response was detected by treating the follicles with 1 µg/ml of extract.

Examples 5 to 6

Activity of Direct Isopropyl (d-iPrOH) Alcohol Extract Obtained from *Chaetoceros* sp. on the Growth of Hair Follicles The experimental protocol previously described was adopted to study the activity of direct-isopropyl alcohol extract obtained from *Chaetoceros* sp. on the growth of hair follicles. In Table 4, the results of a single experiment are reported.

TABLE 4

Growth of hair follicles - elongation expressed as % ratio of the control group performance. (Data from single experiment)

| Example | Sample | Amount | Average | Std. error | Total no. of HFs | ANOVA |
|---|---|---|---|---|---|---|
| 0 | Control | 0 | 100.0 | 4.9 | 14 | — |
| 5 | d-iPrOH | 0.1 µg/ml | 75.7 | 4.6 | 10 | $P < 0.05$ |
| 6 | d-iPrOH | 10.0 µg/ml | 69.1 | 3.6 | 10 | $P < 0.01$ |

Direct isopropyl alcohol extract inhibited hair follicle growth, inducing a reduction of elongation varying from −24% to −31%. The best response was detected by treating the follicles with 10 µg/ml of extract and its results are very significant on a statistical basis.

Examples 7 to 9

Activity of Direct Ethyl Acetate (d-EtAc) Extract Obtained from *Chaetoceros* sp. on the Growth of Hair Follicles The experimental protocol previously described was adopted to study the activity of direct ethyl acetate extract obtained from *Chaetoceros* sp. on the growth of hair follicles. Five replicas were performed by using hair follicles taken from five donors. The reported results were computed by pooling the data recorded from the hair follicles of the responsive donors, however, the number of the responsive donors was reported (Table 5).

TABLE 5

Growth of hair follicles - elongation expressed as % ratio of the control group performance. Data pooled from 3 donors out of 5 tested donors (responsiveness = 60%)

| Example | Sample | Amount | Average | Std. error | Total no. of HFs | ANOVA |
|---|---|---|---|---|---|---|
| 0 | Control | 0 | 100.0 | 2.2 | 52 | |
| 7 | d-EtAc | 0.1 µg/ml | 111.9 | 3.4 | 34 | $P < 0.01$ |
| 8 | d-EtAc | 1.0 µg/ml | 110.2 | 3.5 | 36 | $P < 0.05$ |
| 9 | d-EtAc | 10.0 µg/ml | 112.4 | 3.3 | 35 | $P < 0.01$ |

Direct ethyl acetate extract stimulated the hair follicle growth at all the tested concentrations, inducing an increase of elongation varying from +10% to +12%. All responses resulted significant or very significant on a statistical basis.

Examples 10 to 11

Activity of Direct Ethyl Acetate (d-EtAc) Extract Obtained from *Chaetoceros calcitrans* f. *pumilus* on the Growth of Hair Follicles The experimental protocol previously described was adopted to study the activity of direct ethyl acetate extract obtained from *Chaetoceros calcitrans* f. *pumilus* on the growth of hair follicles. The reported results were obtained from a single donor (Table 6).

TABLE 6

Growth of hair follicles - elongation expressed as % ratio of the control group performance (data from single experiment).

| Example | Sample | Amount | Average | Std. error | Total no. of HFs |
|---|---|---|---|---|---|
| 0 | Control | 0 | 100.0 | 5.0 | 13 |
| 10 | d-EtAc | 0.1 µg/ml | 100.1 | 6.0 | 9 |
| 11 | d-EtAc | 1.0 µg/ml | 110.6 | 7.8 | 9 |

Direct ethyl acetate extract stimulated the hair follicle growth at 1 µg/ml, inducing an increase of elongation of +11%. The results attest the biological activity of the extracts obtained from *C. calcitrans* f. *pumilus* and are consistent with the properties of the extracts previously screened from *Chaetoceros* sp.

Examples 12 to 13

Activity of Sequential Ethanol (s-EtOH) Extract Obtained from *Chaetoceros* sp. on the Growth of Hair Follicles The experimental protocol previously described was adopted to study the activity of sequential ethanol extract obtained from *Chaetoceros* sp. on the growth of hair follicles. Four replicas were performed by using hair follicles taken from four donors. The reported results were computed by pooling the data recorded from the hair follicles of all donors (Table 7).

TABLE 7

Growth of hair follicles - elongation expressed as % ratio of the control group performance. Data pooled from 4 donors out of 4 tested donors (responsiveness = 100%)

| Example | Sample | Amount | Average | Std. error | Total no. of HFs | ANOVA |
|---|---|---|---|---|---|---|
| 0 | Control | 0 | 100.0 | 2.3 | 70 | |
| 12 | s-EtOH | 0.1 µg/ml | 104.2 | 3.0 | 46 | n.s. |
| 13 | s-EtOH | 1.0 µg/ml | 111.9 | 3.5 | 43 | $P < 0.01$ |

Sequential ethanol extract stimulated hair follicle growth preferably at 1 µg/ml, inducing an average increase of elongation of +12%, which resulted highly significant on a statistical basis.

Examples 14 to 15

Activity of Sequential Ethanol (s-EtOH) Extract Obtained from *Chaetoceros calcitrans* f. *pumilus* on the Growth of Hair Follicles The experimental protocol previously described was adopted to study the activity of sequential ethanol extract obtained from *Chaetoceros calcitrans* f. *pumilus* on the growth of hair follicles. The reported results were obtained from a single donor (Table 8).

TABLE 8

Growth of hair follicles - elongation expressed as % ratio of the control group performance.

| Example | Sample | Amount | Average | Std. error | Total no. of HFs | ANOVA |
|---|---|---|---|---|---|---|
| 0 | Control | 0 | 100.0 | 5.0 | 13 | |
| 14 | s-EtOH | 0.1 µg/ml | 90.9 | 7.6 | 9 | n.s. |
| 15 | s-EtOH | 1.0 µg/ml | 117.6 | 8.2 | 7 | P < 0.05 |

Sequential ethanol extract stimulated hair follicle growth preferably at 1 µg/ml, inducing an average increase of elongation of +18%, which resulted significant on a statistical basis.

The results attest that the biological activity of the extracts obtained from *C. calcitrans* f. *pumilus* are consistent with the properties of the extracts previously screened from *Chaetoceros* sp.

Examples 16 to 17

Activity of Direct Methanol (d-MeOH) Extract Obtained from *Thalassiosira* sp. On the Growth of Hair Follicles The experimental protocol previously described was adopted to study the activity of direct methanol extract obtained from *Thalassiosira pseudonana* on the growth of hair follicles. Three replicas were performed by using hair follicles taken from three donors. The reported results were computed by pooling the data recorded from the hair follicles of the responsive donors, however, the number of the responsive donors was reported (Table 9).

TABLE 9

Growth of hair follicles - elongation expressed as % ratio of the control group performance. Data pooled from 2 donors out of 3 tested donors (responsiveness = 66%)

| Example | Sample | Amount | Average | Std. error | Total no. of HFs | ANOVA |
|---|---|---|---|---|---|---|
| 0 | Control | 0 | 100.0 | 3.1 | 36 | |
| 16 | d-MeOH | 0.1 µg/ml | 111.6 | 4.6 | 21 | P < 0.05 |
| 17 | d-MeOH | 1.0 µg/ml | 97.9 | 3.7 | 23 | n.s. |

Direct methanol extract stimulated the hair follicle growth producing an enhanced elongation of +12% in comparison to the control group. The best response was obtained by treating the follicles with extract at 0.1 µg/ml, which resulted significant on a statistical basis.

Examples 18 to 20

Activity of Direct Isopropyl Alcohol Extract (d-iPrOH) Obtained from *Thalassiosira* sp. On the Growth of Hair Follicles The experimental protocol previously described was adopted to study the activity of direct isopropyl alcohol extract obtained from *Thalassiosira pseudonana* on the growth of hair follicles. A single experiment was performed (Table 10).

TABLE 10

Growth of hair follicles - elongation expressed as % ratio of the control group performance (data from single experiment)

| Example | Sample | Amount | Average | Std. error | Total no. of HFs | ANOVA |
|---|---|---|---|---|---|---|
| 0 | Control | 0 | 100.0 | 4.9 | 14 | |
| 18 | d-iProH | 0.1 µg/ml | 77.5 | 8.0 | 9 | P < 0.05 |
| 19 | d-iProH | 1.0 µg/ml | 85.1 | 8.2 | 10 | n.s. |
| 20 | d-iPrOH | 10.0 µg/ml | 87.3 | 4.2 | 10 | n.s. |

Direct isopropyl alcohol extract inhibited hair follicle growth inducing a reduction of elongation varying from −12% to −22%. The best response was detected by treating the follicles with 0.1 µg/ml of extract, and it resulted significant on a statistical basis.

Examples 21 to 23

Activity of Direct Ethyl Acetate (d-EtAc) Extract Obtained from *Thalassiosira* Sp. On the Growth of Hair Follicles The experimental protocol previously described was adopted to study the activity of direct ethyl acetate extract obtained from *Thalassiosira pseudonana* on hair follicle growth. Five replicas were performed by using hair follicles taken from five donors. The reported results were computed by pooling the data recorded from the hair follicles of the responsive donors, however, the number of the responsive donors was reported (Table 11).

TABLE 11

Growth of hair follicles - elongation expressed as % ratio of the control group performance. Data pooled from 4 donors out of 5 tested donors (responsiveness = 80%)

| Example | Sample | Amount | Average | Std. error | Total no. of HFs | ANOVA |
|---|---|---|---|---|---|---|
| 0 | Control | 0 | 100 | 2.2 | 65 | |
| 21 | d-EtAc | 0.1 µg/ml | 95.9 | 2.8 | 38 | n.s. |
| 22 | d-EtAc | 1.0 µg/ml | 115.2 | 3.6 | 44 | P < 0.01 |
| 23 | d-EtAc | 10.0 µg/ml | 106.0 | 2.8 | 46 | n.s. |

The direct ethyl acetate extract stimulated the hair follicle growth preferably at 1 µg/ml, inducing an average increase of elongation of +15%, which resulted highly significant on a statistical basis.

Examples 24 to 25

Activity of Sequential Ethanol (s-EtOH) Extract Obtained from *Thalassiosira* sp. On the Growth of Hair Follicles The experimental protocol previously described was adopted to study the activity of sequential ethanol extract obtained from *Thalassiosira pseudonana* on the growth of hair follicles. Four replicas were performed by using hair follicles taken from four donors. The reported results were computed by pooling the data recorded from the hair follicles of the responsive donors, however, the number of the responsive donors was reported.

TABLE 12

Growth of hair follicles - elongation expressed as % ratio of the control group performance. Data pooled from 3 donors out of 4 tested donors (responsiveness = 75%)

| Example | Sample | Amount | Average | Std. error | Total no. of HFs | ANOVA |
|---|---|---|---|---|---|---|
| 0 | Control | 0 | 100.0 | 2.9 | 52 | — |
| 24 | s-EtOH | 0.1 µg/ml | 112.2 | 3.3 | 31 | $P < 0.01$ |
| 25 | s-EtOH | 1.0 µg/ml | 110.5 | 3.7 | 28 | $P < 0.05$ |

Sequential ethanol extract stimulated hair follicle growth, producing an elongation increase varying from +10% to +12% in comparison to the control group. Both treatments produced results significant on a statistical basis. The best response was detected by treating the hair follicles at 0.1 µg/ml, inducing an average increase of elongation of +12%, which resulted highly significant on a statistical basis.

Examples 26 to 27

Activity of Direct Methanol Extract (d-MeOH) Obtained from *Monodus* sp. on the Growth of Hair Follicles The experimental protocol previously described was adopted to study the activity of direct methanol extract obtained from *Monodus subterraneus* on the growth of hair follicles. Three replicas were performed by using hair follicles taken from three donors. The reported results were computed by pooling the data recorded from the hair follicles of the responsive donors, however, the number of the responsive donors was reported (Table 13).

TABLE 13

Growth of hair follicles - elongation expressed as % ratio of the control group performance. Data pooled from 2 donors out of 3 tested donors (responsiveness = 66%)

| Example | Sample | Amount | Average | Std. error | Total no. of HFs | ANOVA |
|---|---|---|---|---|---|---|
| 0 | Control | 0 | 100.0 | 2.2 | 32 | |
| 26 | d-MeOH | 0.1 µg/ml | 117.7 | 3.2 | 23 | $P < 0.001$ |
| 27 | d-MeOH | 1.0 µg/ml | 114.8 | 3.8 | 23 | $P < 0.01$ |

Direct methanol extract stimulated hair follicle growth producing an enhanced elongation varying from +15% to +18% in comparison to the control group. Both results are statistically significant; however, the best response was detected by treating the follicles at 0.1 µg/ml inducing an average increase of elongation of +18%, which resulted highly significant on a statistical basis.

Examples 28 to 30

Activity of Direct Ethanol Extract (d-EtOH) Obtained from *Monodus* sp. on the Growth of Hair Follicles The experimental protocol previously described was adopted to study the activity of direct ethanol extract obtained from *Monodus subterraneus* on the growth of hair follicles. The experiment was performed by treating the hair follicles with three treatment concentrations, 0.1 µg/ml, 1.0 µg/ml and 10.0 µg/ml respectively. The results are reported in Table 14.

TABLE 14

Growth of hair follicles - elongation expressed as % ratio of the control group performance (Data from single experiment)

| Example | Sample | Amount | Average | Std. error | Total no. of HFs | ANOVA |
|---|---|---|---|---|---|---|
| 0 | Control | 0 | 100 | 4.7 | 18 | |
| 28 | d-EtOH | 0.1 µg/ml | 99.8 | 3.7 | 11 | n.s. |
| 29 | d-EtOH | 1.0 µg/ml | 106.4 | 3.8 | 12 | n.s. |
| 30 | d-EtOH | 10.0 µg/ml | 125.0 | 6.8 | 11 | $P < 0.001$ |

The results attest the strong stimulation performed by the extract at 10 µg/ml of concentration, which produced a growth increase of +25% in comparison to control.

Examples 31 to 33

Activity of Direct Ethyl Acetate Extract (d-EtAc) Obtained from *Monodus* sp. on the Growth of Hair Follicles The experimental protocol previously described was adopted to study the activity of direct ethyl acetate extract obtained from *Monodus subterraneus* on the growth of hair follicles. Three replicas of this experiment were performed by using hair follicles taken from three donors. The reported results were computed by pooling the data recorded from the hair follicles of the responsive donors, however, the number of the responsive donors was reported (Table 15).

TABLE 15

Growth of hair follicles - elongation expressed as % ratio of the control group performance. Data pooled from 3 donors out of 3 tested donors (responsiveness = 100%)

| Example | Sample | Amount | Average | Std. error | Total no. of HFs | ANOVA |
|---|---|---|---|---|---|---|
| 0 | Control | 0 | 100.0 | 2.3 | 49 | |
| 31 | d-EtAc | 0.1 µg/ml | 111.1 | 3.9 | 34 | $P < 0.05$ |
| 32 | d-EtAc | 1.0 µg/ml | 110.7 | 3.7 | 33 | $P < 0.05$ |
| 33 | d-EtAc | 10.0 µg/ml | 110.2 | 3.9 | 20 | n.s. |

Direct ethyl acetate extract stimulated hair follicle growth with similar intensity at all treatment concentrations, however, only at 0.1-1.0 µg/ml the results achieved statistical significance, inducing an average increase of elongation of +11%.

Examples 34 to 35

Activity of Sequential Ethanol Extract (s-EtOH) Obtained from *Monodus* sp. on the Growth of Hair Follicles The experimental protocol previously described was adopted to study the activity of sequential ethanol extract obtained from *Monodus subterraneus*, on the growth of hair follicles. Two replicas of this experiment were performed by using hair follicles taken from two donors. The reported results were computed b pooling the data recorded from the hair follicles of the responsive donors, however, the number of the responsive donors was reported (Table 16).

TABLE 16

Growth of hair follicles - elongation expressed as % ratio of the control group performance. Data pooled from 2 donors out of 2 tested donors (responsiveness = 100%)

| Example | Sample | Amount | Average | Std. error | Total no. of HFs | ANOVA |
|---|---|---|---|---|---|---|
| 0 | Control | 0 | 100.0 | 2.9 | 33 | |
| 34 | s-EtOH | 0.1 µg/ml | 118.1 | 4.4 | 24 | $P < 0.01$ |
| 35 | s-EtOH | 1.0 µg/ml | 115.2 | 5.6 | 22 | $P < 0.05$ |

Sequential ethanol extract stimulated the hair follicle growth producing an elongation increase varying from +15% to +18% in comparison to the control group. Both tested treatments produced results significant on a statistical basis. The preferable treatment was performed at 0.1 µg/ml, inducing an average increase of elongation of +18%, which resulted highly significant on a statistical basis.

Examples 36 to 37

Activity of Direct Methanol Extract (d-MeOH) Obtained from *Chlorococcum* sp. on the Growth of Hair Follicles The experimental protocol previously described was adopted to study the activity of direct methanol extract obtained from *Chlorococcum* sp. on the growth of hair follicles. Three replicas of this experiment were performed by using hair follicles taken from three donors. The reported results were computed by pooling the data recorded from the hair follicles of the responsive donors, however, the number of the responsive donors was reported (Table 17).

TABLE 17

Growth of hair follicles - elongation expressed as % ratio of the control group performance. Data pooled from 3 donors out of 3 tested donors (responsiveness = 100%)

| Example | Sample | Amount | Average | Std. error | Total no. of HFs | ANOVA |
|---|---|---|---|---|---|---|
| 0 | Control | 0 | 100.0 | 1.8 | 50 | |
| 36 | d-MeOH | 0.1 µg/ml | 109.5 | 3.7 | 32 | $P < 0.05$ |
| 37 | d-MeOH | 1.0 µg/ml | 108.5 | 3.4 | 33 | $P < 0.05$ |

Direct methanol extract stimulated hair follicle growth, producing an elongation enhancement varying from +8.5% to +9.5% in comparison to the control group. All results are statistically significant; however, the best response was detected by treating the follicles at 0.1 µg/ml.

Examples 38 to 39

Activity of Direct Ethanol Extract (d-EtOH) Obtained from *Chlorococcum* sp. on the Growth of Hair Follicles The experimental protocol previously described was adopted to study the activity of direct ethanol extract obtained from *Chlorococcum* sp. on the growth of hair follicles. The experiment was performed by treating the hair follicles with two treatment concentrations, 0.1 µg/ml and 1 µg/ml, respectively. The results are reported in Table 18.

TABLE 18

Growth of hair follicles - elongation expressed as % ratio of the control group performance. (Data from single experiment)

| Example | Sample | Amount | Average | Std. error | Total no. of HFs | ANOVA |
|---|---|---|---|---|---|---|
| 0 | Control | 0 | 100.0 | 4.7 | 18 | |
| 38 | d-EtOH | 0.1 µg/ml | 109.6 | 6.4 | 11 | n.s. |
| 39 | d-EtOH | 1.0 µg/ml | 118.8 | 4.5 | 11 | $P < 0.05$ |

The results attest the strong stimulation performed by the extract at 1.0 µg/ml of concentration, which produced a growth increase of +19% in comparison to control. The response assumes statistical significance ($P<0.05$).

Examples 40 to 42

Activity of Direct Isopropyl Alcohol (d-iPrOH) Extract Obtained from *Chlorococcum* sp. on the Growth of Hair Follicles The experimental protocol previously described was adopted to study the activity of direct isopropyl alcohol extract obtained from *Chlorococcum* sp. on the growth of hair follicles. The reported data were obtained from a single experiment (Table 19).

TABLE 19

Growth of hair follicles - elongation expressed as % ratio of the control group performance. Data from a single donor

| Example | Sample | Amount | Average | Std. error | Total no. of HFs | ANOVA |
|---|---|---|---|---|---|---|
| 0 | Control | 0 | 100.0 | 4.9 | 14 | |
| 40 | d-iPrOH | 0.1 µg/ml | 94.0 | 7.3 | 10 | n.s. |
| 41 | d-iPrOH | 1.0 µg/ml | 85.0 | 5.2 | 10 | n.s. |
| 42 | d-IPrOH | 10.0 µg/ml | 81.2 | 4.4 | 11 | $P < 0.05$ |

Direct isopropyl alcohol extract inhibited hair follicle growth inducing a reduction of elongation varying from −6% to −19% in comparison to the control group. The best response was detected by treating the follicles with 10 µg/ml of extract and its results were significant on a statistical basis.

Examples 43 to 45

Activity of Direct Ethyl Acetate Extract (d-EtAc) Obtained from *Chlorococcum* sp. on the Growth of Hair Follicles The experimental protocol previously described was adopted to study the activity of direct ethyl acetate extract obtained from *Chlorococcum* sp. on the growth of hair follicles. The experiments were replicated three times using hair follicles taken from three donors. The reported results were computed by pooling the data recorded from the hair follicles of the responsive donors, however, the number of the responsive donors was reported (Table 20).

TABLE 20

Growth of hair follicles - elongation expressed as % ratio of the control group performance. Data pooled from 3 donors out of 3 tested donors (responsiveness = 100%)

| Example | Sample | Amount | Average | Std. error | Total no. of HFs | ANOVA |
|---|---|---|---|---|---|---|
| 0 | Control | 0 | 100.0 | 1.9 | 50 | |
| 43 | d-EtAc | 0.1 µg/ml | 114.1 | 3.6 | 34 | P < 0.01 |
| 44 | d-EtAc | 1.0 µg/ml | 105.8 | 3.1 | 34 | n.s. |
| 45 | d-EtAc | 10.0 µg/ml | 104.5 | 3.8 | 23 | n.s. |

Direct ethyl acetate extract stimulated hair follicle growth at all treatment concentrations, however, the best response was detected at 0.1 µg/ml, inducing a growth increase of +14%. The response is highly significant on a statistical basis.

Examples 46 to 47

Activity of Direct Ethyl Acetate Extract (d-EtAc) Obtained from *Chlorococcum minutum* on the Growth of Hair Follicles The experimental protocol previously described was adopted to study the activity of direct ethyl acetate extract obtained from *Chlorococcum minutum* on the growth of hair follicles. The reported results were obtained by testing hair follicle taken from a single donor (Table 21).

TABLE 21

Growth of hair follicles - elongation expressed as % ratio of the control group performance (data from single experiment)

| Example | Sample | Amount | Average | Std. error | Total no. of HFs |
|---|---|---|---|---|---|
| 0 | Control | 0 | 100.0 | 5.0 | 13 |
| 46 | d-EtAc | 0.1 µg/ml | 109.7 | 5.4 | 11 |
| 47 | d-EtAc | 1.0 µg/ml | 107.7 | 5.1 | 12 |

Direct ethyl acetate extract stimulated hair follicle growth producing an elongation increase varying from +8% to +10% in comparison to the control group. The preferable treatment was performed at 0.1 µg/ml, inducing an average increase of elongation of +10%.

The results attest that the biological activity of the extracts obtained from *C. minutum* are consistent with the properties of the extracts previously screened from *Chlorococcum* sp.

Examples 48 to 50

Activity of Sequential Ethanol Extract (s-EtOH<EtAc) Obtained from *Chlorococcum* sp. on the Growth of Hair Follicles The experimental protocol previously described was adopted to study the activity of sequential ethanol extract obtained from *Chlorococcum* sp. on the growth of hair follicles. The experiments were replicated twice using hair follicles taken from two donors. The reported results were computed by pooling the data recorded from the hair follicles of the responsive donors, however, the number of the responsive donors was reported (Table 22).

TABLE 22

Growth of hair follicles - elongation expressed as % ratio of the control group performance. Data pooled from 2 donors out of tested donors (responsiveness = 100%)

| Example | Sample | Amount | Average | Std. error | Total no. of HFs | ANOVA |
|---|---|---|---|---|---|---|
| 0 | Control | 0 | 100.0 | 2.3 | 34 | |
| 48 | s-EtOH | 0.1 µg/ml | 118.5 | 4.3 | 22 | P < 0.001 |
| 49 | s-EtOH | 1.0 µg/ml | 116.7 | 3.2 | 21 | P < 0.001 |
| 50 | s-EtOH | 10.0 µg/ml | 100.4 | 4.8 | 11 | n.s. |

Sequential ethanol extract stimulated hair follicle growth, producing an elongation increase varying from +17% to +19% in comparison to the control group. The treatments at both concentrations of 0.1 µg/ml and 1 µg/ml produced responses highly significant on a statistical basis. The preferable treatment was performed at 0.1 µg/ml, inducing an average increase of elongation of +19%, which resulted highly significant on a statistical basis.

B. Activity on Hair Growth—General Conclusions

The presented examples attest the intense activity of the studied extracts on the metabolism of hair follicles. These activities were detected in broad and direct extracts as in the case of direct methanolic extracts as well as in sequentially prepared extracts, which includes compounds separated according to the solvent polarity gradient. All results attest that several actives are included in the same microalgae material, potentially suitable to produce opposite effects on the hair follicles. The extract activity, indeed, depends on the adopted preparation protocol. Different solvents can be selected in order to extract compounds having specific activities. The sequential extracts prepared by using different solvents show that they include different actives despite they were obtained from the same microalgae cell material (Table 23).

Table 23

Synthesis of Disclosed Activities Produced by the Studied Extracts on Hair Growth Elongation Expressed as % Ratio of the Control Group Performance (Best Average Responses)

TABLE 23

Synthesis of disclosed activities produced by the studied extracts on hair growth elongation expressed as % ratio of the control group performance (best average responses)

| Extract code | d-MeOH | d-EtOH | d-iPrOH | d-EtAc | s-EtOH < d-EtAc |
|---|---|---|---|---|---|
| *Chaetoceros* Sp. | +10% | | −24% | +12% | +12% |
| *Chaetoceros calcitrans* | | +20% | | +11% | +12%/+18% |
| *Thalassiosira psudonana* | +8% | | −22% | +15% | +12% |

TABLE 23-continued

Synthesis of disclosed activities produced by the studied extracts on hair growth elongation expressed as % ratio of the control group performance (best average responses)

| Extract code | d-MeOH | d-EtOH | d-iPrOH | d-EtAc | s-EtOH < d-EtAc |
|---|---|---|---|---|---|
| *Monodus subterraneus* | +17% | +25% | | +12% | +18% |
| *Chlorococcum* sp. | +10% | +19% | −19% | +14% | +19% |
| *Chlorococcum minutum* | | | | +10% | |

C. Activity on Melanogenesis Disclosed for the Considered Microalgae Extracts

Melanocytes are the cell species responsible for melanogenesis both in the skin and the hair follicles. Melanin is the pigment accumulated in hair and skin and susceptible to be quantitatively modulated in response to sunlight exposition, aging processes and eventually also to pathological events.

The possibility to modulate melanogenesis represents, therefore, a relevant opportunity in cosmetics, for the relevance that body appearance assumes in social life, but also for the effective preservation of a healthy and young-looking condition of skin and hair.

The activity of the microalgae extracts on melanogenesis was studied by screening the preparations ex-vivo human skin in order to attest the effect also on the whole tissue.

Assay Performed on Ex-Vivo Human Skin Culture

Organ cultures of full thickness human skin were performed starting from a skin sample, exciding cylindrical pieces of about 7 mm in diameter and culturing them up to day 6. The adopted culture medium was a modified William-E, and it was renewed at day three of the tissue culture. Samples of the sequential extracts were air-dried and then solved in a quantity of DMSO suitable to obtain a final concentration of 1 and 10 µg/ml. On a daily basis, 4 µl of these extract preparations were topically applied to the cultured skin samples. After six days of organ culture, histological sections were prepared from the skin samples, and quantitative changes of melanin content were investigated by adopting the Fontana-Masson staining technique. The melanin quantification was obtained by image analysis of microphotographs of each histological skin section.

Examples 51 to 56

Activity of Three-Step Sequential Extracts Obtained from *Monodus* sp. on Melanogenesis Three-step sequential extracts (ethyl acetate>ethanol>water) were prepared from *Monodus subterraneus*. These extracts were screened by treating human skin samples as described above. The experiment was replicated twice using skin samples taken from two donors. The results shown in Table 24 were computed by pooling the data recorded from both replicas.

TABLE 24

Activity of sequential extracts obtained from *Monodus* sp. on melanogenesis in ex-vivo cultured human skin. Melanin content expressed as % ratio of the control group performance. Data pooled from 2 out of 2 tested donors (responsiveness = 100%)

| Example | Sample | Amount | Average | Std. error | No. of samples | ANOVA |
|---|---|---|---|---|---|---|
| 0 | Control | 0 | 100.0 | 5.4 | 24 | |
| 51 | d-EtAc | 1.0 µg/ml | 92.2 | 3.7 | 24 | n.s. |
| 52 | d-EtAc | 10 µg/ml | 113.0 | 6.4 | 24 | n.s. |
| 53 | s-EtOH | 1.0 µg/ml | 75.3 | 3.7 | 24 | $P < 0.01$ |
| 54 | s-EtOH | 10 µg/ml | 86.2 | 4.9 | 24 | $P < 0.05$ |
| 55 | s-Water | 1.0 µg/ml | 80.5 | 6.1 | 24 | $P < 0.01$ |
| 56 | s-Water | 10 µg/ml | 101.2 | 5.3 | 24 | n.s. |

The results attest that both the sequential ethanol extract and the sequential water extract performed a melanogenesis inhibition, which led to a reduction in melanin content varying from −19% to −25% in comparison to the control. The results are significant or highly significant on a statistical basis. On the contrary, direct ethyl acetate extract did not perform any significant modulation of melanogenesis.

Examples 57 to 62

Activity of Three-Step Sequential Extracts Obtained from *Chlorococcum* sp. on Melanogenesis Three-step sequential extracts (ethyl acetate>ethanol>water) were prepared from *Chlorococcum* sp. These extracts were screened by treating human skin samples as described above. The experiment was replicated twice using skin samples taken from two donors. The results shown in table 25 were computed by pooling the data recorded from both replicas.

TABLE 25

Activity of sequential extracts obtained from *Chlorococcum* sp. on melanogenesis in ex-vivo cultured human skin. Melanin content expressed as % ratio of the control group performance. Data pooled from 2 out of 2 tested donors (responsiveness = 100%)

| Example | Sample | Amount | Average | Std. error | No. of samples | ANOVA |
|---|---|---|---|---|---|---|
| 0 | Control | 0 | 100.0 | 5.4 | 24 | |
| 57 | d-EtAc | 1.0 µg/ml | 90.7 | 4.9 | 24 | n.s. |
| 58 | d-EtAc | 10 µg/ml | 85.9 | 4.3 | 24 | $P < 0.05$ |
| 59 | s-EtOH | 1.0 µg/ml | 85.2 | 2.5 | 24 | $P < 0.05$ |
| 60 | s-EtOH | 10 µg/ml | 80.8 | 3.4 | 24 | $P < 0.01$ |
| 61 | s-Water | 1.0 µg/ml | 102.5 | 5.5 | 24 | n.s. |
| 62 | s-Water | 10 µg/ml | 99.9 | 4.4 | 24 | n.s. |

The results attest that both the direct ethyl acetate extract and the sequential ethanol extract performed an inhibition of melanogenesis, which led to a reduction of melanin content varying from −8% to −19% in comparison to the control. The results are significant or highly significant on a statistical basis. On the contrary, the sequential water extract did not modulate melanogenesis.

Examples 63 to 74

Activity of Three-Step Sequential Extracts Obtained from *Chlorococcum minutum* and *Chaetoceros calcitrans* f. *pumilus* on melanogenesis Three-step sequential extracts (ethyl acetate>ethanol>water) were prepared respectively from *Chlorococcum minutum* (C) and *Chaetoceros calcitrans* f. *pumilus* (K). These extracts were screened by treating human skin samples as described above. The results are shown in Table 26.

TABLE 26

Activity of sequential extracts obtained from *Chlorococcum minutum* (C) and *Chaetoceros calcitrans* f. *pumilus* (K) on melanogenesis in ex-vivo cultured human skin. Melanin content expressed as % ratio of the control group performance.

| Example | Strain | Sample | Amount | Average | Std. error | No. of samples | ANOVA |
|---|---|---|---|---|---|---|---|
| 0 | | Control | 0 | 100.0 | 7.3 | 21 | |
| 63 | C | d-EtAc | 1.0 µg/ml | 105.9 | 5.6 | 10 | n.s. |
| 64 | C | d-EtAc | 10 µg/ml | 95.6 | 6.1 | 10 | n.s. |
| 65 | C | s-EtOH | 1.0 µg/ml | 86.7 | 4.7 | 10 | n.s. |
| 66 | C | s-EtOH | 10 µg/ml | 81.4 | 5.2 | 10 | $P < 0.05$ |
| 67 | C | s-Water | 1.0 µg/ml | 107.7 | 5.3 | 10 | n.s. |
| 68 | C | s-Water | 10 µg/ml | 82.7 | 4.4 | 10 | $P < 0.05$ |
| 69 | K | d-EtAc | 1.0 µg/ml | 78.5 | 9.1 | 10 | $P < 0.05$ |
| 70 | K | d-EtAc | 10 µg/ml | 78.2 | 4.5 | 10 | $P < 0.05$ |
| 71 | K | s-EtOH | 1.0 µg/ml | 78.0 | 5.1 | 10 | $P < 0.05$ |
| 72 | K | s-EtOH | 10 µg/ml | 69.7 | 3.4 | 10 | $P < 0.01$ |
| 73 | K | s-Water | 1.0 µg/ml | 88.2 | 9.9 | 10 | n.s. |
| 74 | K | s-Water | 10 µg/ml | 79.3 | 6.5 | 10 | $P < 0.05$ |

The results attest that the sEtOH and sWater extracts obtained from *Chlorococcum* inhibited melanogenesis, reducing the melanin content from −13% to −19% in comparison to the control. The results are significant on a statistical basis for both treatments at 10 µg/ml. All extracts prepared from *Chaetoceros* produced a relevant melanogenesis inhibition, varying from −12% to −30% in comparison to the control. The results are significant or very significant on a statistical basis; the more intense response was detected by treating the skin with sEtOH extract at 10 µg/ml, which produced a reduction in melanin content of −30%.

Examples 75 to 82

Activity of Direct Methanol Extracts Obtained from *Chlorococcum Minutum*, *Monodus subterraneus*, *Thalassiosira pseudonana* and *Chaetoceros calcitrans* f. *pumilus* on melanogenesis Direct methanol extracts (MeOH) were prepared from *Chlorococcum minutum* (C), *Monodus subterraneus* (M), *Thalassiosira pseudonana* (T) and *Chaetoceros calcitrans* f. *pumilus* (K), respectively. These extracts were screened by treating human skin samples as described above. The results are shown in Table 27.

TABLE 27

Activity of methanol extracts obtained from *Chlorococcum minutum* (C) and *Chaetoceros calcitrans* f. *pumilus* (K) on melanogenesis in ex-vivo cultured human skin. Melanin content expressed as % ratio of the control group performance.

| Example | Strain | Sample | Amount | Average | Std. error | No. of samples | ANOVA |
|---|---|---|---|---|---|---|---|
| 0 | | Control | 0 | 100.0 | 7.2 | 10 | |
| 75 | C | d-MeOH | 1.0 µg/ml | 68.2 | 4.5 | 10 | $P < 0.01$ |
| 76 | C | d-MeOH | 10 µg/ml | 81.4 | 7.6 | 10 | n.s. |
| 77 | M | d-MeOH | 1.0 µg/ml | 83.8 | 7.9 | 10 | n.s. |
| 78 | M | d-MeOH | 10 µg/ml | 84.1 | 5.9 | 10 | n.s. |
| 79 | T | d-MeOH | 1.0 µg/ml | 74.6 | 9.0 | 10 | $P < 0.05$ |
| 80 | T | d-MeOH | 10 µg/ml | 69.2 | 7.2 | 10 | $P < 0.01$ |
| 81 | K | d-MeOH | 1.0 µg/ml | 95.6 | 7.0 | 10 | n.s. |
| 82 | K | d-MeOH | 10 µg/ml | 81.5 | 7.7 | 10 | n.s. |

The results attest that all extracts performed a melanogenesis inhibition, which led to a reduction of melanin content varying from −5% to −32% in comparison to the control. The results are very significant on a statistical basis for both treatments with extract obtained from *Chlorococcum* at 1 µg/ml (−32% in comparison to control) and with extract from *Thalassiosira* at 10 µg/ml (−31% in comparison to control).

D. Microalgae Activity Disclosed on Primary Skin Cells

The microalgae extracts were screened for their activity on primary fibroblasts or keratinocytes isolated from human skin. The aim of the screening plan was to investigate potential activities of stimulation on collagen type I and hyaluronate synthesis. Collagen I is a protein and hyaluronate is a glycosaminoglycan, both of them are important components of the dermis which undergo significant quantity and quality reductions as an effect of skin aging.

Culture media supplemented with microalgae extracts were screened on primary cell cultures in order to evaluate the microalgae activity on the cell synthesis of collagen and hyaluronate.

Modulation of Collagen Synthesis Studied by Means of Primary Dermal Fibroblasts

The experimental procedure was based on the following steps:

Primary fibroblasts were seeded in 96 wells microplates at a density of 20,000 cells/cm$^2$;

After 24 h of cultivation, the culture medium was displaced with supplemented culture media prepared by adding 0.1 µg/ml, 1.0 µg/ml or 10 µg/ml of extracts obtained from the aforementioned microalgae strains. Two series of 8 wells were dedicated to the screening of each supplemented medium. Two series of 8 wells were maintained as a control group and cultured in standard medium;

After 48-72 h of cultivation, the fibroblasts were close to confluence, and the collagen quantification was performed by means of ELISA directly on the culture plate. The adopted ELISA protocol was specifically set up for these experiments, however, a conceptually similar procedure was reported by Jenkins et al. (2007, BMC Cardiovascular Disorders, 7: 13). For each treated group, 8 wells were submitted to MTT assay in order to estimate the final cell density, while the remaining 8 wells were submitted to ELISA in order to estimate the produced collagen. The same procedure was performed on the control group. The ELISA values divided by the estimated cell density were assumed as normalised collagen quantity index. The data obtained from the treated groups were expressed as percent ratio of the values expressed by the control group.

Examples 83 to 88

Activity of Direct Methanol (d-MeOH) Extract Obtained from *Chaetoceros* sp., *Monodus* sp. and *Chlorococcum* sp. on Fibroblast Collagen Synthesis The d-MeOH extracts obtained from *Chaetoceros* sp. (K), *Monodus subterraneus* (M) and *Chlorococcum* sp. (C) were screened in order to assess their modulating effect on collagen synthesis performed by dermal fibroblasts. Primary fibroblasts were treated as described above and, unpredictably, a relevant collagen synthesis modulation was detected in response to the treatments. The results are shown in Table 28.

TABLE 28

Activity on the dermis detected by treating primary fibroblasts with d-MeOH extracts at 0.1 and 10 µg/ml - Quantity of collagen expressed as % ratio of the control group

| Example | Sample | St. | Amount | Average | Std. error | No. of wells | ANOVA |
|---|---|---|---|---|---|---|---|
| 0 | Control | — | 0 | 100.0 | 1.7 | 8 | |
| 83 | d-MeOH | K | 0.1 µg/ml | 135.9 | 10.7 | 7 | P < 0.01 |
| 84 | d-MeOH | K | 10 µg/ml | 177.2 | 6.4 | 8 | P < 0.01 |
| 85 | d-MeOH | M | 0.1 µg/ml | 150.2 | 11.3 | 8 | P < 0.01 |
| 86 | d-MeOH | M | 10 µg/ml | 158.2 | 14.1 | 8 | P < 0.01 |
| 87 | d-MeOH | C | 0.1 µg/ml | 161.9 | 11.2 | 8 | P < 0.01 |
| 88 | d-MeOH | C | 10 µg/ml | 194.2 | 12.2 | 8 | P < 0.01 |

The extracts obtained from *Chaetoceros*, *Monodus* and *Chlorococcum* intensely stimulated the collagen synthesis at all concentrations of treatment. The results are highly significant on a statistical basis.

Examples 89 to 94

Activity of Direct Ethanol (d-EtOH) Extract and Sequential Water (s-Water) Extract Obtained from *Chaetoceros* sp. on Fibroblast Collagen Synthesis The direct ethanol and sequential water extracts obtained from *Chaetoceros* sp. by performing a two-step extraction were screened in order to assess their modulating effect on the fibroblast collagen synthesis. The extracts were screened on fibroblast cultures according to the protocol previously described. The results are reported in Table 29.

TABLE 29

Activity on the dermis detected by treating primary fibroblasts - Quantity of collagen expressed as % ratio of the control group

| Example | Sample | Amount | Average | Std. error | No. of wells | ANOVA |
|---|---|---|---|---|---|---|
| 0 | Control | 0 | 100.0 | 3.9 | 8 | — |
| 89 | d-EtOH | 0.1 µg/ml | 163.4 | 4.3 | 8 | P < 0.01 |
| 90 | d-EtOH | 1.0 µg/ml | 132.6 | 11.0 | 8 | P < 0.01 |
| 91 | d-EtOH | 10 µg/ml | 137.2 | 5.4 | 8 | P < 0.01 |
| 92 | s-Water | 0.1 µg/ml | 143.5 | 8.9 | 8 | P < 0.01 |
| 93 | s-Water | 1.0 µg/ml | 115.6 | 7.5 | 8 | n.s. |
| 94 | s-Water | 10 µg/ml | 128.9 | 6.1 | 8 | P < 0.01 |

The extracts obtained from *Chaetoceros* produced intense collagen synthesis stimulation at almost all treatment concentrations. The results are highly significant on a statistical basis.

Examples 95 to 102

Activity of Direct Ethyl Acetate (d-EtAc) Extract, Sequential Ethanol (sEtOH) and Sequential Water (s-Water) Extract Obtained from *Chaetoceros calcitrans* f. *Pumilus* on Fibroblast Collagen Synthesis The three-step sequential extracts (d-EtAc>s-EtOH>s-Water) obtained from *Chaetoceros calcitrans* f. *pumilus* were screened in order to assess their modulating effect on fibroblast collagen synthesis. The extracts were screened on fibroblast cultures according to the protocol described above. The results are reported in Table 30.

TABLE 30

Activity on the dermis detected by treating primary fibroblasts - Quantity of collagen expressed as % ratio of the control group

| Example | Sample | Amount | Average | Std. error | No. of wells | ANOVA |
|---|---|---|---|---|---|---|
| 0 | Control | 0 | 100.0 | 3.5 | 8 | — |
| 95 | d-EtAc | 0.1 µg/ml | 107.5 | 1.9 | 8 | n.s. |
| 96 | d-EtAc | 1.0 µg/ml | 105.7 | 6.2 | 8 | n.s. |
| 97 | d-EtAc | 10 µg/ml | 124.6 | 2.6 | 8 | P < 0.01 |
| 98 | s-EtOH | 0.1 µg/ml | 100.6 | 12.0 | 8 | n.s. |
| 99 | s-EtOH | 1.0 µg/ml | 120.7 | 2.9 | 8 | P < 0.01 |
| 100 | s-Water | 0.1 µg/ml | 112.2 | 3.2 | 8 | n.s. |
| 101 | s-Water | 1.0 µg/ml | 102.0 | 5.5 | 8 | n.s. |
| 102 | s-Water | 10 µg/ml | 102.4 | 2.9 | 8 | n.s. |

All extracts stimulated the production of collagen, increasing the collagen synthesis from +12% (s-Water extract) to +25% (d-EtAc extract). However, the most relevant effects were obtained by treating the cells with dEtAc 10 µg/ml, which increased the collagen synthesis of +25%, and by treating with sEtOH 1 µg/ml which increased the synthesis of +21% in comparison the control group. Both these results are very significant on a statistical basis (P<0.01). The sequential water extract at 0.1 µg/ml stimulated the collagen production up to +12% as well.

Examples 103 to 108

Activity of Direct Methanol (d-MeOH) Extract and Sequential Ethanol (s-EtOH) Extract Obtained from *Chaetoceros calcitrans* f. *pumilus* on Fibroblast Collagen Synthesis Direct methanol extract (d-MeOH) and two-step sequential ethanol extract (d-EtAc>s-EtOH) obtained from *Chaetoceros calcitrans* f. *pumilus* were screened in order to assess their modulating effect on fibroblast collagen synthesis. The extracts were screened on fibroblast cultures according to the protocol previously described. The results are reported in Table 31.

TABLE 31

Activity on dermis detected by treating primary fibroblasts - Quantity of collagen expressed as % ratio of the control group

| Example | Sample | Amount | Average | Std. error | No. of wells | ANOVA |
|---|---|---|---|---|---|---|
| 0 | Control | 0 | 100.0 | 4.8 | 8 | — |
| 103 | d-MeOH | 0.1 µg/ml | 116.2 | 3.3 | 8 | P < 0.01 |
| 104 | d-MeOH | 1.0 µg/ml | 113.2 | 2.7 | 8 | P < 0.01 |
| 105 | d-MeOH | 10 µg/ml | 118.0 | 4.2 | 8 | P < 0.01 |
| 106 | s-EtOH | 0.01 µg/ml | 106.7 | 2.5 | 8 | n.s. |
| 107 | s-EtOH | 0.1 µg/ml | 112.7 | 3.5 | 8 | P < 0.01 |
| 108 | s-EtOH | 1.0 µg/ml | 116.5 | 3.3 | 8 | P < 0.01 |

Both screened extracts increased the collagen synthesis. S-EtOH induced the best response at a concentration of 1.0 µg/ml, increasing the collagen synthesis by +16%, while d-MeOH extract induced the best response at a concentration 10 µg/ml, increasing the collagen synthesis by +18%. These results are very significant on a statistical basis (P<0.01).

Examples 109 to 114

Activity of Direct Ethanol (d-EtOH) Extract and Sequential Water (s-Water) Extract Obtained from *Thalassiosira* sp. on Fibroblast Collagen Synthesis The direct ethanol and sequential-water extracts obtained from *Thalassiosira pseudonana* by performing a two-step extraction were screened in order to assess their modulating effect on fibroblast collagen synthesis. The extracts were screened on fibroblast cultures according to the protocol previously described. The results are reported in Table 32.

TABLE 32

Activity on the dermis detected by treating primary fibroblasts - Quantity of collagen expressed as % ratio of the control group

| Example | Sample | Amount | Average | Std. error | No. of wells | ANOVA |
|---|---|---|---|---|---|---|
| 0 | Control | 0 | 100.0 | 3.9 | 8 | — |
| 109 | d-EtOH | 0.1 µg/ml | 127.4 | 22.1 | 8 | P < 0.01 |
| 110 | d-EtOH | 1.0 µg/ml | 148.9 | 6.0 | 8 | P < 0.01 |
| 111 | d-EtOH | 10 µg/ml | 148.4 | 5.4 | 8 | P < 0.01 |
| 112 | s-Water | 0.1 µg/ml | 127.2 | 3.6 | 8 | P < 0.05 |
| 113 | s-Water | 1.0 µg/ml | 161.1 | 3.8 | 8 | P < 0.01 |
| 114 | s-Water | 10 µg/ml | 172.5 | 10.1 | 8 | P < 0.01 |

The extracts obtained from *Thalassiosira* produced an intense collagen synthesis stimulation at all treatment concentrations. The results are highly significant on a statistical basis.

Examples 115 to 120

Activity of Direct Ethanol (d-EtOH) Extract and Sequential Water (s-Water) Extract Obtained from *Chlorococcum* sp. on Fibroblast Collagen Synthesis The direct ethanol and sequential water extracts obtained from *Chlorococcum* sp. by performing a two-step extraction were screened in order to assess their modulating effect on fibroblast collagen synthesis. The extracts were screened on fibroblast cultures according to the protocol previously described. The results are reported in Table 33:

TABLE 33

Activity on the dermis detected by treating primary fibroblasts - Quantity of collagen expressed as % ratio of the control group

| Example | Sample | Amount | Average | Std. error | No. of wells | ANOVA |
|---|---|---|---|---|---|---|
| 0 | Control | 0 | 100.0 | 7.3 | 8 | — |
| 115 | d-EtOH | 0.1 µg/ml | 161.5 | 12.0 | 8 | P < 0.01 |
| 116 | d-EtOH | 1.0 µg/ml | 153.0 | 12.4 | 8 | P < 0.01 |
| 117 | d-EtOH | 10 µg/ml | 186.9 | 8.8 | 8 | P < 0.01 |
| 118 | s-Water | 0.1 µg/ml | 182.1 | 10.8 | 8 | P < 0.01 |
| 119 | s-Water | 1.0 µg/ml | 187.2 | 13.5 | 8 | P < 0.01 |
| 120 | s-Water | 10 µg/ml | 150.6 | 10.8 | 8 | P < 0.01 |

The extracts obtained from *Chlorococcum* sp. produced an intense collagen synthesis stimulation at all treatment concentrations. The results are highly significant on a statistical basis.

Examples 121 to 129

Activity of Three-Step Sequential Extracts Obtained from *Monodus* sp. on Fibroblast Collagen Synthesis The three-step sequential extracts (d-EtAc>s-EtOH>s-Water) obtained from *Monodus subterraneus* were screened in order to assess their modulating effect on fibroblast collagen synthesis according to the screening protocol previously described. The results are reported in Table 34:

TABLE 34

Activity on the dermis detected by treating primary fibroblasts - Quantity of collagen expressed as % ratio of the control group

| Example | Sample | Amount | Average | Std. error | No. of wells | ANOVA |
|---|---|---|---|---|---|---|
| 0 | Control | 0 | 100 | 6.1 | 8 | — |
| 121 | d-EtAc | 0.1 µg/ml | 97.8 | 5.7 | 8 | n.s. |
| 122 | d-EtAc | 1.0 µg/ml | 105.8 | 3.3 | 8 | n.s. |
| 123 | d-EtAc | 10 µg/ml | 110.5 | 5.0 | 8 | n.s. |
| 124 | s-EtOH | 0.1 µg/ml | 106.4 | 5.4 | 8 | n.s. |
| 125 | s-EtOH | 1.0 µg/ml | 112.8 | 6.7 | 8 | n.s. |
| 126 | s-EtOH | 10 µg/ml | 124.0 | 6.4 | 8 | P < 0.01 |
| 127 | s-Water | 0.1 µg/ml | 113.6 | 6.9 | 8 | n.s. |
| 128 | s-Water | 1.0 µg/ml | 143.2 | 4.0 | 7 | P < 0.01 |
| 129 | s-Water | 10 µg/ml | 133.8 | 4.0 | 7 | P < 0.01 |

The sequential ethanol and sequential water extracts obtained from *Monodus* produced an intense collagen synthesis stimulation. The treatment with 1.0 µg/ml of s-EtOH extract induced a +24% increase in collagen synthesis, while the treatment with 1.0 µg/ml and 10 µg/ml of s-Water extract, respectively, increased the collagen synthesis by +43% and +33%. The results are highly significant on a statistical basis. The d-EtAc extract produced a moderate stimulation of the collagen synthesis, up to +10% in comparison to the control group.

Modulation of Hyaluronate Synthesis Studied by Means of Primary Dermal Fibroblasts.

Primary fibroblast cultures treated with microalgae extracts were screened according to the following protocol:
- 15,000 cells/well were seeded in 24 well plates and cultured in 500 µl/well of complete culture medium;
- as soon as the cells reached about 80-90% of the confluence, the medium was withdrawn and substituted by 500 µl/well of FBS-free medium supplemented with the microalgal extracts. The control group received the FBS-free medium without supplementation;
- after 16 hours of treatment, the medium was recovered and processed for the Hyaluronan ELISA test (Corgenix hyaluronan ELISA kit) while the plate containing the cell layers was submitted to the MTT test for cell number estimation;

The hyaluronate quantification obtained for each cell group was normalised on the MTT data and expressed as percentage ratio related to control group performance.

Examples 130 to 132

Activity of Extracts Obtained from *Monodus* sp. and *Chlorococcum* sp. on Fibroblast Hyaluronate Synthesis The described experimental protocol was adopted for the purpose of screening the direct ethyl acetate extract and the sequential water extract obtained from *Monodus subterraneus* (M) in comparison to the direct ethyl acetate extract obtained from *Chlorococcum* sp. (C). The fibroblast treatments were performed at 1.0 µg/ml in three replicas. The results are reported in Table 35.

TABLE 35

Activity on primary fibroblasts - Quantity of hyaluronate expressed as % ratio of the control group

| Example | Sample | St. | Amount | Average | Std. error | No. of wells | ANOVA |
|---|---|---|---|---|---|---|---|
| 0 | Control | — | 0 | 100.0 | 3.1 | 3 | |
| 130 | d-EtAc | C | 1.0 µg/ml | 113.3 | 7.3 | 3 | n.s. |
| 131 | d-EtAc | M | 1.0 µg/ml | 146.0 | 15.6 | 3 | P < 0.05 |
| 132 | s-Water | M | 1.0 µg/ml | 117.3 | 11.5 | 3 | n.s. |

The treated fibroblasts performed an increased production of hyaluronic acid from +13% to +46% in comparison to the control group. The activity expressed by the *Monodus* direct ethyl acetate extract resulted significant on a statistical basis.

Examples 133 to 134

Activity of Direct Ethyl Acetate (d-EtAc) and Sequential Ethanol (s-EtOH) Extracts Obtained from *Chaetoceros calcitrans* f. *pumilus* on Fibroblast Hyaluronate Synthesis The described experimental protocol was adopted for the purpose of screening the direct ethyl acetate extract and the sequential water extract obtained from *Chaetoceros calcitrans* f. *pumilus*. The fibroblast treatments were performed at 10 µg/ml in three replicas. The results are reported in Table 36.

TABLE 36

Activity on primary fibroblasts - Quantity of hyaluronate expressed as % ratio of the control group

| Example | Sample | Amount | Average | Std. error | No. of wells | ANOVA |
|---|---|---|---|---|---|---|
| 0 | Control | 0 | 100 | 4.37 | 3 | |
| 133 | d-EtAc | 10 µg/ml | 117.9 | 2.36 | 3 | P < 0.05 |
| 134 | s-EtOH | 10 µg/ml | 106.8 | 9.1 | 3 | n.s. |

The fibroblasts treated with EtAc extract increased the production of hyaluronic acid of +18% in comparison to the control group. The activity expressed by the *Chaetoceros* direct ethyl acetate extract resulted significant on a statistical basis (P<0.05).

Modulation of Hyaluronate Synthesis Studied by Means of Primary Keratinocytes

The screening analysis was performed on primary keratinocyte cultures treated with microalgae extracts according to the following protocol:
  25,000 cells/well were seeded in 24 well plates and cultured in 500 µl/well of complete culture medium;
  As soon as the cells overcame the 50% of the confluence, the medium was withdrawn and substituted by 500 µl/well medium supplemented with the microalgal extract. The control groups received standard medium without supplementation;
  After 16 hours of treatment, the medium was recovered and processed for Hyaluronan ELISA test (Corgenix hyaluronan ELISA kit) while the remaining cell layers were submitted to MTT test for the cell number estimation;

The hyaluronate quantification obtained for each cell group was normalised on the MTT data and expressed as percentage ratio related to control group performance.

Examples 135 to 136

Activity of Extracts Obtained from *Monodus* sp. and *Chlorococcum* sp. on Keratinocyte Hyaluronate Synthesis The described experimental protocol was adopted for the purpose of screening the direct ethyl acetate extract obtained from *Monodus subtraneus* (M) in comparison to the direct ethyl acetate extract obtained from *Chlorococcum* sp. (C). The keratinocyte treatments were performed at 1.0 µg/ml in three replicas. The results are reported in Table 37.

TABLE 37

Activity on primary keratinocytes - Quantity of hyaluronate expressed as % ratio of the control group

| Example | Sample | St. | Amount | Average | Std. error | No. of wells | ANOVA |
|---|---|---|---|---|---|---|---|
| 0 | Control | — | 0 | 100.0 | 1.4 | 3 | — |
| 135 | d-EtAc | C | 1.0 µg/ml | 102.9 | 0.9 | 3 | n.s. |
| 136 | d-EtAc | M | 1.0 µg/ml | 111.3 | 4.0 | 3 | P < 0.05 |

The direct ethyl acetate extract obtained from *Monodus* stimulated the fibroblasts to increase their synthesis of collagen by +11%. The response is significant also on a statistical basis (P<0.05).

Conclusive Remarks

The foregoing experiments disclose that the extracts obtained from *Monodus subterraneus*, *Chaetoceros calcitrans* and *Chlorococcum* sp. are biologically active in the synthesis of hyaluronate performed by skin fibroblasts and keratinocytes. This strongly suggests that these extracts can be proposed as effective ingredients for anti-aging and anti-photoaging formulations.

E. Microalgae Activity Disclosed on Ex-Vivo Dermis and Epidermis

The data hereinafter reported attest that the screened microalgae extracts can modulate the synthesis of basic proteins and GAG components performed by fibroblasts and keratinocytes. However, we further investigated the microalgae properties by performing experiments on ex-vivo full thickness human skin. The following experiments are oriented at:
  confirming the relevant collagen synthesis stimulation also in ex-vivo skin by studying the collagen quantification in histological sections;
  exploring the capability of the microalgae extracts to modulate the differentiation of keratinocytes in the skin epidermis by studying the presence of involucrin in the stratum corneum via Western Blot analysis (WB).

The relevant role of collagen with regard to the composition of the dermis has already been discussed. The stratum corneum of the skin is the superficial part of the tissue, composed by dead corneocytes, which fulfil the relevant functions of preventing water loss from the skin and the penetration of organisms or undesired compounds from the external environment. The integrity and functionality of the horny layer is essential in order to maintain an appropriate skin moisture and defend the body from pathogens. The skin needs moisture to stay smooth and supple, and the retention of moisture becomes increasingly difficult as the body ages. On the other hand, the altered composition or thickness of the stratum corneum is the cause or part of several common skin disorders, i.e. xerosis, or true pathologies, i.e. psoriasis. A reduced horny layer thickness may induce skin dehydration, while the opposite problem may lead to hyperkeratosis. The cell component of the stratum corneum is the corneocyte, which represents the final differentiated stage of the epidermal keratinocyte. The involucrin is a recognized protein marker involved in the keratinisation process at the basis of the keratinocytes differentiation. The involucrin synthesis can be studied in order to define if experimental treatment increases or reduces the keratinization of the epidermis. Both these activities can be of interest for applications in cosmetics and therapeutics.

Activity of *Monodus* and *Chlorococcum* Sequential Water Extracts on the Dermal Collagen Synthesis Studied on Ex-Vivo Human Skin Culture Examples 137 to 140

Activity of Sequential Extracts Obtained from *Monodus* sp. and *Chlorococcum* sp. on the Collagen Synthesis in Cultured Ex-Vivo Skin Sequential water extracts were prepared by means of tree-step sequential extraction from *Monodus subterraneus* (M) and *Chlorococcum* sp. (C) cell materials. These extracts were solved in pure DMSO at the two different final concentrations of 1 and 10 µg/ml. Organ cultures of full thickness human skin were prepared as reported for examples 58 to 63 with regard to the modulation of melanogenesis on cultured ex-vivo skin. The cultured skin samples were treated daily with topical application 4 µl of these microalgae preparations diluted in DMSO. After six days of organ culture, histological sections were prepared from the skin samples, and the quantitative changes of collagen protein were investigated by mounting histological preparations treated according to the Miller staining technique. Microphotographs of the histological skin sections were taken, and the dermis collagen quantification was obtained by submitting the microphotographs to computerized image analysis. The results are shown in Table 38.

TABLE 38

Activity of sequential water extract obtained from *Monodus* sp. and *Chlorococcum* sp. on the collagen synthesis in cultured ex-vivo human skin - Quantity of collagen expressed as % ratio of the control group performance

| Example | Sample | St. | Amount | Average | Std. error | Samples | ANOVA |
|---|---|---|---|---|---|---|---|
| 0 | Control | — | 0 | 100.0 | 10.3 | 12 | — |
| 137 | s-Water | C | 1.0 µg/ml | 121.5 | 7.1 | 12 | n.s. |
| 138 | s-Water | C | 10 µg/ml | 118.5 | 11.8 | 12 | n.s. |
| 139 | s-Water | M | 1.0 µg/ml | 143.8 | 13.1 | 12 | P < 0.01 |
| 140 | s-Water | M | 10 µg/ml | 143.6 | 9.4 | 11 | P < 0.01 |

The results attest that all sequential water extracts performed a collagen synthesis stimulation with responses varying from between +18% and +44%. The treatments with *Monodus* s-water extract produced responses highly significant on a statistical basis.

Examples 141 to 152

Activity of Sequential Extract Obtained from *Monodus* sp. and *Chlorococcum* sp. on the Involucrin Synthesis in Cultured Ex-Vivo Skin The skin organ culture technique previously described was adopted for the purpose of screening the sequential extracts obtained from *Monodus subterraneus* (M) and from *Chlorococcum* sp. (C) in order to explore their activity on the epidermal stratum corneum. The topical treatments were prepared by solving the dry extracts in DMSO to the final concentrations of 1 µg/ml and 10 µg/ml. The cultured skin samples were treated for six days with these preparations on a daily basis, and then their involucrin content was quantified by means of Western blot analysis. The dermis was almost completely removed from the skin samples prior to preparing the protein extract for Western blot analysis. Processing each experimental group, three skin samples were pooled during the protein extract preparation, and then each protein extract was analyzed in replica by Western blot technique. The responses to the treated tissues are reported in Table 39 as percentage variation of involucrin content in comparison to the control group.

TABLE 39

Activity of sequential water extract obtained from *Chlorococcum* sp. and *Monodus subterraneus* on involucrin synthesis in cultured ex-vivo human skin - Quantity of involucrin expressed as % ratio of the control group performance

| Ex. | Sample | S | Amount | Average | Skin samples pooled in protein extract | Protein extract samples | Activity |
|---|---|---|---|---|---|---|---|
| 0 | Control | — | 0 | 100.0 | 3 | 2 | |
| 141 | d-EtAc | C | 1.0 µg/ml | 122.2 | 3 | 2 | Stimulation |
| 142 | d-EtAc | C | 10 µg/ml | 97.7 | 3 | 2 | n.s. |
| 143 | s-EtOH | C | 1.0 µg/ml | 95.6 | 3 | 2 | weak stimulation |
| 144 | s-EtOH | C | 10 µg/ml | 110.1 | 3 | 2 | strong stimulation |
| 145 | s-Water | C | 1.0 µg/ml | 175.1 | 3 | 2 | strong stimulation |
| 146 | s-Water | C | 10 µg/ml | 138.3 | 3 | 2 | strong stimulation |
| 147 | d-EtAc | M | 1.0 µg/ml | 122.1 | 3 | 2 | Stimulation |
| 148 | d-EtAc | M | 10 µg/ml | 134.6 | 3 | 2 | Strong stimulation |
| 149 | s-EtOH | M | 1.0 µg/ml | 123.9 | 3 | 2 | Stimulation |
| 150 | s-EtOH | M | 10 µg/ml | 104.8 | 3 | 2 | n.s. |

TABLE 39-continued

Activity of sequential water extract obtained from *Chlorococcum* sp. and *Monodus subterraneus* on involucrin synthesis in cultured ex-vivo human skin - Quantity of involucrin expressed as % ratio of the control group performance

| Ex. | Sample | S | Amount | Average | Skin samples pooled in protein extract | Protein extract samples | Activity |
|---|---|---|---|---|---|---|---|
| 151 | s-Water | M | 1.0 µg/ml | 106.1 | 3 | 2 | n.s. |
| 152 | s-Water | M | 10 µg/ml | 74.2 | 3 | 2 | Inhibition |

The tested extracts obtained from *Chlorococcum* stimulated the involucrin synthesis from +10% to +75% in comparison to the control group, and the sequential water extract induced the higher response (+75%).

The direct ethyl acetate and sequential ethanol extracts obtained from *Monodus* stimulated the involucrin synthesis from +22% to +34%, while the sequential water extract reduced the involucrin synthesis.

F. Activity on Cell Proliferation Disclosed for the Considered Microalgae Extracts Skin cell proliferation represents a relevant issue for at least two reasons: the preservation of melanocytes and wound healing.

Normal human melanocytes are located in the basal layer of the epidermis and rarely undergo mitosis. Their density can decrease in some epidermal structures when the body ages, as, for instance, in the hair follicle. The cosmetic industry is therefore very interested in products suitable to promote melanocyte activity and proliferation. Furthermore, some skin disorders, i.e. vitiligo, are due to acquired depigmentation caused by melanocyte death, therefore compounds active in melanocyte proliferation may be effective in therapies against similar problems.

At the same time, the proliferation of other skin cells is desirable when wounds are produced in the tissue. Increasing the cell reproduction rate, the wound healing process is accelerated by reducing the risk of infection. Products supporting the wound healing process are required both for the treatment of accidental injuries and for dermatologic or aesthetic surgery.

Some extracts obtained from the aforementioned microalgae were screened in order to assess their effects on cell proliferation. Surprisingly, they disclosed to perform a relevant stimulation on the cell reproduction rate when adopted at the right concentration and on sensitive cell species.

Examples 153 to 160

Activity of Direct Methanol (d-MeOH) Extract Obtained from *Chaetoceros* sp., *Thalassiosira* sp., *Monodus* sp. and *Chlorococcum* sp. on Proliferation of Melanocyte-Like Cells The following experiment was designed to study the effect of methanolic extracts (d-MeOH) obtained from *Chaetoceros* sp. (K), *Thalassiosira pseudonana* (T), *Chlorococcum* sp. (C) and *Monodus subterraneus* (M).

B16V cells were selected as a representative model for melanocyte responsiveness. 96 well plates were seeded with 7,500 cell/well and the cells were cultured in medium RPMI1640 supplemented with FBS 10% and 4 mM glutamine. After 24 hours of culture, the healthy condition of the cells was verified, and the culture medium was substituted by the experimental media in order to start the treatments. Each treatment was replicated on 6 wells. For each screened extract, the experimental media was prepared by supplementing the standard culture medium by 0.5 µl/ml or, respectively, 0.05 µl/ml of 20.000 µg/ml dry microalgal extract solved in DMSO. The final extract concentrations in these supplemented media resulted in 10 µg/ml and, respectively, 0.1 µg/ml, while the DMSO concentration resulted in 0.05% and 0.005%. Two control groups were treated with standard medium supplemented by 0.05% and, respectively, 0.005% of DMSO. After 3 days of treatment, the culture was stopped and all final cell numbers corresponding to each experimental group was assessed by means of the resazurin assay.

The results are expressed as average percentage variation of the cell density in comparison to the control group and are synthesized in Table 40 below:

TABLE 40

Activity on cell proliferation detected by treating B16V with d-MeOH extracts at 0.1 and 10 µg/ml - The final number of cells is expressed as % ratio of control group performance

| Example | Sample | St. | Amount | Average | Std. error | No. of wells | ANOVA |
|---|---|---|---|---|---|---|---|
| 0 | Control | — | 0 | 100.0 | 1.6 | 6 | — |
| 153 | d-MeOH | K | 0.1 µg/ml | 99.8 | 1.8 | 6 | n.s. |
| 154 | d-MeOH | T | 0.1 µg/ml | 100.5 | 2.2 | 6 | n.s. |
| 155 | d-MeOH | M | 0.1 µg/ml | 98.4 | 2.5 | 6 | n.s. |
| 156 | d-MeOH | C | 0.1 µg/ml | 100.8 | 1.2 | 6 | n.s. |
| 157 | d-MeOH | K | 10 µg/ml | 109.2 | 2.0 | 6 | P < 0.01 |
| 158 | d-MeOH | T | 10 µg/ml | 106.8 | 1.5 | 6 | P < 0.05 |
| 159 | d-MeOH | M | 10 µg/ml | 101.3 | 1.1 | 6 | n.s. |
| 160 | d-MeOH | C | 10 µg/ml | 112.2 | 2.1 | 6 | P < 0.01 |

The results attest that the extracts obtained from *Chaetoceros*, *Thalassiosira*, and *Chlorococcum* stimulated at a concentration of 10 µg/ml cell proliferation in a significant or very significant manner on a statistical basis.

Examples 161 to 169

Activity of Three-Step Sequential Extracts Obtained from *Chlorococcum* Sp. On Fibroblast proliferation The experimental procedure was based on the following steps:

Primary fibroblasts were seeded in 96 wells microplates at a density of 20,000 cells/cm$^2$;

After 24 h of cultivation, the culture medium was displaced with supplemented culture media prepared by adding 0.1 µg/ml, 1 µg/ml or 10 µg/ml of extracts obtained from *Chlorococcum* cell material. 8 wells were dedicated to the screening of each supplemented medium. 8 wells were maintained as control group and cultured in standard medium;

After 48-72 h of cultivation, fibroblast density was assessed by MTT assay and the performance of each experimental group was expressed as average percentage ratio of the control group performance. The results are shown in Table 41:

TABLE 41

Activity on cell proliferation detected by treating primary fibroblasts with sequential extracts obtained from *Chlorococcum* sp. at 0.1, 1 and 10 µg/ml - The final number of cells is expressed as % ratio of control group performance

| Example | Sample | Amount | Average | Std. error | No. of wells | ANOVA |
|---|---|---|---|---|---|---|
| 0 | Control | 0 | 100.0 | 2.8 | 8 | — |
| 161 | d-EtAc | 0.1 µg/ml | 105.9 | 7.9 | 8 | n.s. |
| 162 | d-EtAc | 1.0 µg/ml | 120.3 | 2.6 | 8 | P < 0.01 |
| 163 | d-EtAc | 10 µg/ml | 124.8 | 4.4 | 8 | P < 0.01 |
| 164 | s-EtOH | 0.1 µg/ml | 109.4 | 5.4 | 8 | n.s. |
| 165 | s-EtOH | 1.0 µg/ml | 113.3 | 2.6 | 8 | P < 0.05 |
| 166 | s-EtOH | 10 µg/ml | 93.1 | 5.3 | 8 | n.s. |
| 167 | s-Water | 0.1 µg/ml | 117.4 | 4.7 | 8 | P < 0.01 |
| 168 | s-Water | 1.0 µg/ml | 114.2 | 3.4 | 8 | P < 0.05 |
| 169 | s-Water | 10 µg/ml | 100.3 | 5.1 | 8 | n.s. |

The data attest that all sequential extracts can stimulate cell proliferation if adopted at an opportune concentration. The treatments increased the final cell number from +13% to +25% in comparison to the control group, reaching significance on a statistical basis.

Examples 170 to 178

Activity of Three-Step Sequential Extracts Obtained from *Monodus* sp. on Fibroblast Proliferation The same experimental procedure was adopted to screen the sequential extracts obtained from cell material of *Monodus subterraneus*. The results are shown in Table 42:

TABLE 42

Activity on cell proliferation detected by treating primary fibroblasts with sequential extracts obtained from *Monodus subterraneus* at 0.1, 1, and 10 µg/ml - The final number of cells is expressed as % ratio of control group performance

| Example | Sample | Amount | Average | Std. error | No. of wells | ANOVA |
|---|---|---|---|---|---|---|
| 0 | Control | 0 | 100.0 | 0.9 | 8 | |
| 170 | d-EtAc | 0.1 µg/ml | 105.4 | 2.6 | 8 | n.s. |
| 171 | d-EtAc | 1.0 µg/ml | 112.1 | 2.6 | 8 | P < 0.01 |
| 172 | d-EtAc | 10 µg/ml | 109.0 | 3.3 | 8 | P < 0.05 |
| 173 | s-EtOH | 0.1 µg/ml | 113.0 | 3.6 | 8 | P < 0.01 |
| 174 | s-EtOH | 1.0 µg/ml | 109.7 | 3.7 | 8 | P < 0.05 |
| 175 | s-EtOH | 10 µg/ml | 125.7 | 3.5 | 8 | P < 0.01 |
| 176 | s-Water | 0.1 µg/ml | 126.5 | 3.8 | 8 | P < 0.01 |
| 177 | s-Water | 1.0 µg/ml | 118.7 | 4.4 | 8 | P < 0.01 |
| 178 | s-Water | 10 µg/ml | 123.8 | 3.6 | 8 | P < 0.01 |

The data attest that all sequential extracts stimulate cell proliferation inducing a final cell number increase from +9% to +27% in comparison to the control group, reaching significance on a statistical basis in all cases except the 0.1 µg/ml dEtAc treatment.

G. Activity on Human Adipocyte Lipolysis Disclosed for the Considered Microalgae Extracts In order to evaluate the activity of the aforementioned microalgae on the lipid metabolism, ex-vivo human skin samples were cultured and treated with d-MeOH extracts obtained from *Chaetoceros* sp., *Thalassiosira* sp., *Monodus* sp. and *Chlorococcum* sp.

The responses of the treated tissues, in comparison to the untreated group, were evaluated by measuring the free glycerol released in the culture medium, i.e. the main final product of the lipolytic metabolism.

Examples 179 to 186

Activity of d-MeOH Extracts Obtained from *Chaetoceros* sp., *Thalassiosira* sp., *Monodus* sp. and *Chlorococcum* sp. on Full Thickness Skin Cultures The direct methanol extracts prepared from cell materials of *Chaetoceros* sp. (K), *Thalassiosira pseudonana* (T), *Monodus subterraneus* (M) and *Chlorococcum* sp. (C) were adopted for supplementing samples of modified William's medium E, aimed to be used for culturing full thickness human skin. Each microalgae extract had a final extract concentration of 5 and 50 µg/ml, respectively, in the supplemented media.

The following experimental procedure was adopted in order to assess the activity of the microalgae extracts on the skin lipid metabolism:
  Cylindrical human skin samples, having 7 mm in diameter, were excised from the same donor and plated at a density of 1 sample/well, in 24-well plates with 700 µl/well of standard culture medium;
  After 24 hours of culture, the standard medium was displaced with the experimental media, except for the control samples, which received the standard medium for the first time. Each experimental treatment was administered to four skin samples (in four different wells). The control group comprised four samples as well.
  After 24 hours of treatment, the glycerol released in the media was quantified by using the Free Glycerol Reagent produced by Sigma (code #F6428). 25 µl of medium were taken from each well and put in triplicate in a 96 well plate, 200 µl of free glycerol reagent were added to each well. After 20 minutes of incubation at RT, the plate was read with a microplate-photometer at 540 nm. The free glycerol in the medium was quantified by relying the detected absorbance values on a standard curve of glycerol as reference.

The experimental results expressed as percentage ratio of the control group performance are shown in Table 43.

TABLE 43

Skin lipolysis modulation performed by d-MeOH extracts obtained from *Chaetoceros* sp., *Thalassiosira pseudonana*, *Monodus subterraneus* and *Chlorococcum* sp. - The data are expressed as % ratio of the control group performance

| Example | Sample | Amount | Average | Std. error | No. of wells | ANOVA |
|---|---|---|---|---|---|---|
| 0 | Control | 0 | 100.0 | 14.2 | 4 | |
| 179 | K | 5.0 µg/ml | 136.9 | 10.1 | 4 | P < 0.05 |
| 180 | K | 50 µg/ml | 99.3 | 7.6 | 4 | n.s. |
| 181 | T | 5.0 µg/ml | 147.9 | 9.4 | 4 | P < 0.01 |
| 182 | T | 50 µg/ml | 109.3 | 16.8 | 4 | n.s. |
| 183 | M | 5.0 µg/ml | 141.1 | 3.8 | 4 | P < 0.05 |
| 184 | M | 50 µg/ml | 123.7 | 16.3 | 4 | n.s. |
| 185 | C | 5.0 µg/ml | 142.4 | 1.5 | 4 | P < 0.05 |
| 186 | C | 50 µg/ml | 152.9 | 14.3 | 4 | P < 0.01 |

The experimental results attest that all extracts stimulated the lipolysis if used at a suitable concentration, increasing the free glycerol release from +23% to +53% in comparison to the control group.

The extracts obtained from the diatoms (*Chaetoceros* and *Thalassiosira*), having high dry weights (cf. Table 1), induced a statistically significant or very significant response at 5 μg/ml, while they did not produce any effect at 50 μg/ml.

The treatments with *Monodus* and *Chlorococcum* extracts, instead, stimulated the skin lipolysis at all treatment concentrations despite the response detected by treating the skin with 50 μg/ml of *Monodus* extract did not match the statistical significance.

The screened microalgae extracts disclosed to perform an intense modulation of the skin lipolysis. They are suitable to be included in formulations for the treatment of fat tissue disorders, both for aesthetic and therapeutic purposes.

Examples 187 to 194

Activity of d-MeOH Extracts Obtained from *Chaetoceros* sp., *Thalassiosira* sp., *Monodus* sp. and *Chlorococcum* sp. on Full Thickness Skin Cultures The experimental procedure described for the previous experiment was replicated in order to confirm the biological activity of the methanolic preparations obtained from the considered microalgae. The data obtained are shown in Table 44.

TABLE 44

Skin lipolysis modulation performed by d-MeOH extracts obtained from *Chaetoceros* sp., *Thalassiosira pseudonana*, *Monodus subterraneus* and *Chlorococcum* sp. - The data are expressed as % ratio of the control group performance

| Example | Sample | Amount | Average | Std. error | No. of wells | ANOVA |
|---|---|---|---|---|---|---|
| 0 | Control | 0 | 100.0 | 15.7 | 4 | |
| 187 | K | 5.0 μg/ml | 192.0 | 15.8 | 4 | P < 0.01 |
| 188 | K | 50 μg/ml | 104.3 | 10.0 | 4 | n.s. |
| 189 | T | 5.0 μg/ml | 109.3 | 17.5 | 4 | n.s. |
| 190 | T | 50 μg/ml | 102.0 | 23.5 | 4 | n.s. |
| 191 | M | 5.0 μg/ml | 195.3 | 24.3 | 4 | P < 0.01 |
| 192 | M | 50 μg/ml | 173.4 | 10.3 | 4 | P < 0.01 |
| 193 | C | 5.0 μg/ml | 214.8 | 11.0 | 4 | P < 0.01 |
| 194 | C | 50 μg/ml | 202.2 | 13.9 | 4 | P < 0.01 |

The data confirm the biological activity of the extracts stimulating the lipolysis, with particular intensity for the *Monodus* and *Chlorococcum* extracts, which increased the release of free glycerol at all treatment concentrations. The stimulation of lipolysis resulted for these two extracts from +73% to +114% in comparison to the control, always matching the high significance on a statistical basis.

The extracts obtained from the diatoms confirmed to be more active at 5 μg/ml than at higher concentrations. Although both preparations stimulated lipolysis, only *Chaetoceros* met the significance on a statistical basis.

Examples 195 to 198

Activity of d-MeOH Extracts Obtained from *Thalassiosira* sp. and *Chlorococcum* sp. on Full Thickness Skin Cultures The experimental procedure described for the previous experiment was replicated in order to confirm the biological activity of the methanolic preparations obtained from *Thalassiosira pseudonana* and *Chlorococcum* sp. The data obtained are shown in Table 45.

TABLE 45

Skin lipolysis modulation performed by d-MeOH extracts obtained from *Thalassiosira pseudonana* and *Chlorococcum* sp. - The data are expressed as % ratio of the control group performance

| Example | Sample | Amount | Average | Std. error | No. of wells | ANOVA |
|---|---|---|---|---|---|---|
| 0 | Control | 0 | 100.0 | 10.9 | 4 | |
| 195 | T | 5.0 μg/ml | 127.0 | 25.5 | 4 | n.s. |
| 196 | T | 50 μg/ml | 140.4 | 10.0 | 4 | n.s. |
| 197 | C | 5.0 μg/ml | 116.6 | 30.1 | 4 | n.s. |
| 198 | C | 50 μg/ml | 169.8 | 24.5 | 4 | P < 0.01 |

The data confirm the biological activity of the extracts stimulating the lipolysis. The increase of lipolysis reached a peak of +40% in response to the treatment with *Thalassiosira* extract, while it resulted in +70% in response to the treatment with *Chlorococcum* extract.

Examples 199 to 206

Activity of d-MeOH Extracts Obtained from *Chaetoceros* sp., *Chaetoceros calcitrans* f. *pumilus, Chlorococcum* sp. and *Chorococcum minutumon* in Full Thickness Skin Cultures The experimental procedure described for the previous experiment was replicated in order to compare the biological activity of different algae strains of the same genus. New methanol extracts were prepared from dried biomass of *Chaetoceros calcitrans* f. *pumilus* (also known as CCAP 1010/11 and deposited at the Culture Collection of Algae and Protozoa managed by the Scottish Association for Marine Science) and from dried biomass of *Chlorococcum minutum* (also known as CCAP 213/7 and deposited at the Culture Collection of Algae and Protozoa). These new extracts were used in comparison with the previous preparations obtained from *Chaetoceros* sp. and from *Chlorococcum* sp. (both of unknown origin) for treatment of human full thickness skin samples in order to study their effects on lipolysis. The data obtained are shown in Table 46.

TABLE 46

Skin lipolysis modulation performed by d-MeOH extracts obtained from *Chaetoceros calcitrans* f. *pumilus* (K-CCAP1010/11), *Chaetoceros* sp. (K), *Chloroccum minutum* (C-CCAP213/7) and *Chlorococcum* sp. (C) - The data are expressed as % ratio of the control group performance

| Example | Sample | Amount | Average | Std. error | No. of wells | ANOVA |
|---|---|---|---|---|---|---|
| 0 | Control | 0 | 100.0 | 12.5 | 4 | |
| 199 | K | 5.0 μg/ml | 118.7 | 11.6 | 4 | n.s. |
| 200 | K | 50 μg/ml | 115.5 | 7.6 | 4 | n.s. |
| 201 | K ccap1010/11 | 5.0 μg/ml | 136.2 | 3.8 | 4 | P < 0.05 |

TABLE 46-continued

Skin lipolysis modulation performed by d-MeOH extracts obtained from
Chaetoceros calcitrans f. pumilus (K-CCAP1010/11), Chaetoceros sp.
(K), Chloroccum minutum (C-CCAP213/7) and Chlorococcum sp. (C) -
The data are expressed as % ratio of the control group performance

| Example | Sample | Amount | Average | Std. error | No. of wells | ANOVA |
|---|---|---|---|---|---|---|
| 202 | K ccap1010/11 | 50 µg/ml | 109.6 | 10.3 | 4 | n.s. |
| 203 | C | 5.0 µg/ml | 139.9 | 8.8 | 4 | P < 0.05 |
| 204 | C | 50 µg/ml | 117.1 | 3.0 | 4 | n.s. |
| 205 | Cccap213/7 | 5.0 µg/ml | 123.2 | 12.9 | 4 | n.s. |
| 206 | Cccap213/7 | 50 µg/ml | 118.1 | 17.5 | 4 | n.s. |

The treatments increased the free glycerol release from +9% to +40%, confirming the stimulation of lipolysis performed by the strains belonging to both genera. The more active preparations, however, resulted in this case obtained from *Choirococcum* sp. and *Chaetocerous calcitrans* f. *pumilus* CCAP1010/11, which produced responses significant also on a statistical basis.

The invention claimed is:

1. A method for stimulating hair growth in a subject in need thereof, comprising topically applying to said subject a composition comprising from 0.001 to 35% by weight of an extract of *Monodus* sp., based on dry matter content of the extract, wherein said extract is an ethanol, methanol, or ethyl acetate extract obtained by contacting *Monodus* sp. with a solvent selected from ethanol, methanol, or ethyl acetate to provide an extract dissolved in solvent and a residue, separating the extract dissolved in solvent from the residue, and recovering the ethanol, methanol, or ethyl acetate extract of *Monodus* sp.

2. The method according to claim 1, comprising administering an effective amount of the extract for modulating melanogenesis in human hair.

3. The method according to claim 1, comprising administering an effective amount of the extract for improving and stimulating growth of human hair and hair follicles.

4. The method according to claim 1, comprising administering an effective amount of the extract for treating and inhibiting hair loss.

5. The method according to claim 1, comprising administering an effective amount of the extract for improving and stimulating melanocyte proliferation in hair.

6. A method for stimulating hair growth in a subject in need thereof, comprising topically applying to said subject a composition comprising from 0.001 to 35% by weight of an extract of *Chaetoceros* sp., based on dry matter content of the extract, wherein the extract is an ethanol, methanol, or ethyl acetate extract of *Chaetoceros* sp. obtained by contacting said *Chaetoceros* sp. with ethanol, methanol, or ethyl acetate to provide an extract dissolved in solvent and a residue, separating the extract dissolved in the solvent from the residue, and recovering the ethanol, methanol, or ethyl acetate extract of *Chaetoceros* sp.

7. The method according to claim 6, comprising administering an effective amount of the extract for improving and stimulating growth of human hair and hair follicles.

8. The method according to claim 6, comprising administering an effective amount of the extract for treating and inhibiting hair loss.

9. The method according to claim 6, wherein the extract of *Chaetoceros* sp. is obtained by adding the solvent to a biomass of *Chaetoceros* sp., to provide a residual cell material, and separating the extract from the residual cell material.

10. A method for modulating melanogenesis in human skin and/or the horny layer in the human epidermis, improving and stimulating at least one of collagen synthesis in the human dermis, glucosaminoglycans synthesis in human skin, keratinocyte differentiation in the human epidermis, the proliferation of dermal and epidermal cells and wound healing, melanocyte proliferation, and lipolysis, and treating and inhibiting skin aging comprising topically applying to a subject in need thereof, a composition comprising from 0.001 to 35% by weight of an extract of *Monodus* sp., and/or *Chlorococcum* sp., based on dry matter content of the extract, wherein said extract is a C1-C4 aliphatic alcohol or ethyl acetate extract of *Monodus* sp., and/or *Chlorococcum* sp. obtained by contacting said *Monodus* sp. and/or *Chlorococcum* sp. with a solvent selected from a C1-C4 aliphatic alcohol or ethyl acetate to provide an extract dissolved in solvent and a residue; separating the extract dissolved in the solvent from the residue; and recovering the C1-C4 aliphatic alcohol or ethyl acetate extract of *Monodus* sp. and/or *Chlorococcum* sp.

11. The method according to claim 10, comprising administering an effective amount of the extract for modulating melanogenesis in human skin and/or the horny layer in the human epidermis.

12. The method according to claim 10, comprising administering an effective amount of the extract for improving and stimulating at least one of collagen synthesis in the human dermis, glucosaminoglycans synthesis in human skin, keratinocyte differentiation in the human epidermis, the proliferation of dermal and epidermal cells and wound healing, melanocyte proliferation, and lipolysis.

13. The method according to claim 10, comprising administering an effective amount of the extract for treating and inhibiting skin aging.

14. A method for inhibiting hair growth in a subject in need thereof, comprising topically applying to skin and/or a subcutis area in need thereof a composition comprising from 0.001% to 35% by weight of an extract of *Monodus* sp. and/or *Chlorococcum* sp. based upon dry matter content of the extract, wherein the extract is an isopropyl alcohol extract, and wherein the extract is obtained by contacting *Monodus* sp. and/or *Chlorococcum* sp. with isopropyl alcohol to provide a dissolved extract and a residue; separating the dissolved extract from the residue; and recovering the isopropyl alcohol extract of *Monodus* sp. and/or *Chlorococcum* sp.

* * * * *